United States Patent [19]
Nakasuji

[11] Patent Number: 5,892,224
[45] Date of Patent: Apr. 6, 1999

[54] APPARATUS AND METHODS FOR INSPECTING WAFERS AND MASKS USING MULTIPLE CHARGED-PARTICLE BEAMS

[75] Inventor: Mamoru Nakasuji, Yokohama, Japan

[73] Assignee: Nikon Corporation, Tokyo, Japan

[21] Appl. No.: 855,736

[22] Filed: May 9, 1997

[30] Foreign Application Priority Data

May 22, 1996 [JP] Japan ................................. 8-127405
May 13, 1996 [JP] Japan ................................. 8-117750
Oct. 31, 1996 [JP] Japan ................................. 8-289786

[51] Int. Cl.$^6$ ................................. H01J 37/28; G01N 23/22
[52] U.S. Cl. ................................. 250/310; 250/307; 250/397
[58] Field of Search ................................. 250/310, 307, 250/397

[56] References Cited

U.S. PATENT DOCUMENTS 5,430,292  7/1995  Honjo et al. ................................. 250/310

OTHER PUBLICATIONS

Fujioka et al., "A Fully Computer-Controlled Scanning Electron Microscope," *J. Electron Microsc.* 35:215–219 (1986).
Jones et al., "Microstructures for Particle Beam Control," *J. Vac. Sci. Technol.* B 6:2023–2027 (1988).
Meisburger et al., "Requirements and Performance of an Electron–Beam Column Designed for X–Ray Mask Inspection," *J. Vac. Sci. Technol.* B 9:3010–3014 (1991).

*Primary Examiner*—Jack I. Berman
*Attorney, Agent, or Firm*—Klarquist Sparkman Campbell Leigh & Whinston, LLP

[57] ABSTRACT

Apparatus and methods are disclosed for inspecting masks, reticles, and other patterned samples used in microlithography. The apparatus and methods are useful for detecting, at high speed and high accuracy, any defects in the pattern defined by the sample. Multiple charged-particle beams (e.g., electron beams) scannably irradiated simultaneously on respective loci in an irradiation region of a surface of the sample. A charged-particle detector is situated so as to detect charged particles propagating, during the irradiation, from the loci. The charged-particle detector produces data on whether or not the pattern in the irradiated region has any defects compared to a reference pattern. The detectors can be situated so as to receive charged particles reflected from the irradiated region, charged particles passing through the irradiated region, or secondary electrons produced from irradiating the loci. An electrode plate, preferably defining multiple apertures each dedicated to receiving charged particles originating at a respective locus, is used to attract the charged particles toward the detectors.

70 Claims, 12 Drawing Sheets

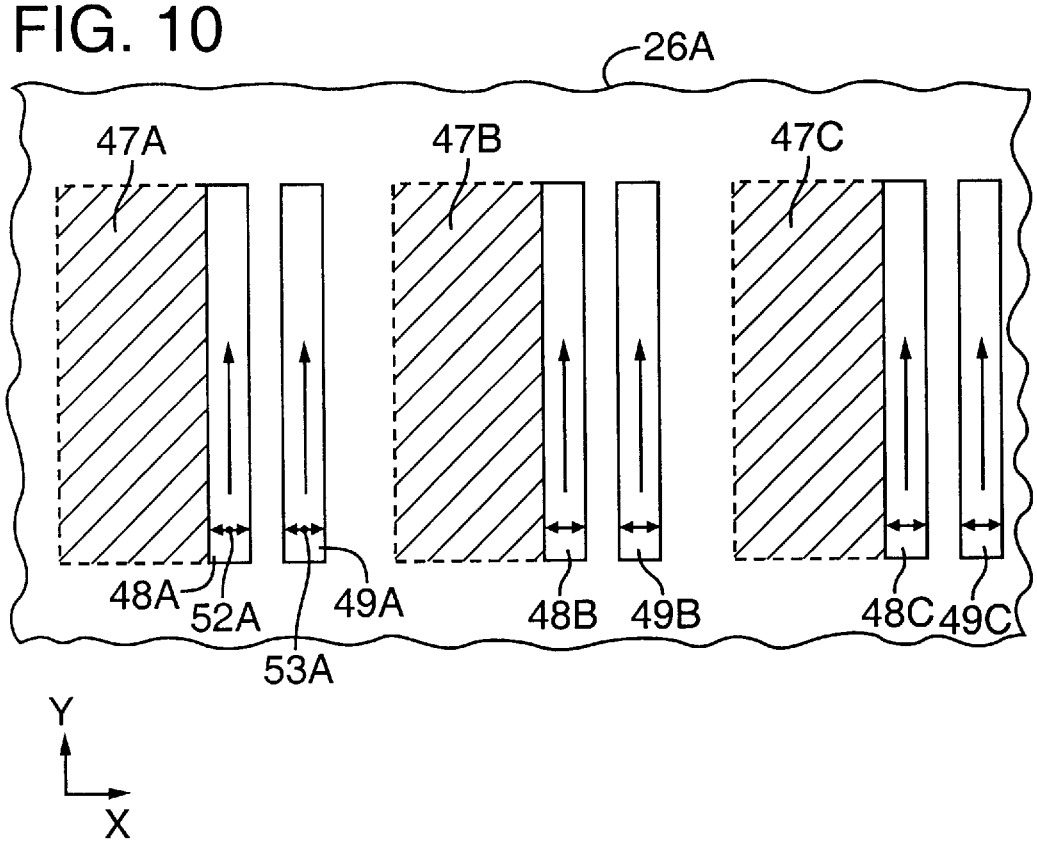

APPARATUS AND METHODS FOR INSPECTING WAFERS AND MASKS USING MULTIPLE CHARGED-PARTICLE BEAMS

FIELD OF THE INVENTION

This invention is related to microlithography, i.e., apparatus and methods by which a pattern defined on a mask or reticle ("mask") is transferred to a sensitive substrate such as a semiconductor wafer. More specifically, the invention pertains to systems and methods for inspecting masks and wafers used in microlithography, especially systems and methods employing a charged-particle beam for inspecting the mask or wafer.

BACKGROUND OF THE INVENTION

After fabrication, a mask or reticle ("mask") should be inspected before use to make sure that the mask accurately defines the desired pattern. This is because any defects in the mask pattern will be transferred to the substrate (e.g., wafer) during use of the mask in microlithography. It is also desirable to perform an inspection of a wafer at suitable moments during manufacture of devices on the wafer. As used herein, a "sample" for inspection purposes can be a wafer, mask, reticle, or analogous structure having a pattern that is the subject of the inspection.

Conventionally, a type of scanning electron microscope (SEM) has been used to inspect samples to detect pattern defects. The surface of the sample is scanned using a single finely drawn electron beam. Impingement of the beam on the sample generates secondary electrons. A pattern defect at a location on the sample is detected by comparing an intensity signal of the secondary electrons to, for example, a reference signal corresponding to the same location on the pattern.

The conventional SEM as summarized above exhibits high resolution compared to an optical microscope. However, because only one very narrow electron beam is used for scanning, a long time is required to scan the entire surface of the sample. This undesirably results in low throughput. If the scanning speed of the electron beam is increased to reduce the scanning time per sample, the signal-to-noise ratio (S/N ratio) of the secondary electron signal sensed by the detector can be too small for reliable detection of errors on the sample.

Many masks define patterns made up of identical portions repeated many times at a fixed pitch over the entire pattern. Each identical portion can be scanned relative to a reference signal. However, because the mask is conventionally scanned by one electron beam, the periodicity of the pattern defined by the mask cannot be exploited and throughput is not improved.

SUMMARY OF THE INVENTION

In view of the foregoing, an object of the present invention is to provide a pattern-defect inspection system for performing inspection of pattern defects on a mask, reticle, wafer, or other suitable sample at high speed and high accuracy.

Another object is to provide a pattern-defect inspection system for performing pattern-defect inspections of samples at a high throughput using a charged-particle beam.

Yet another object is to provide a pattern-defect inspection system for inspecting, at high throughput, a sample surface defining a pattern comprising multiple periodic pattern portions.

Yet another object is to provide a sample-inspection system exhibiting a shorter scan time and thus increased throughput compared to prior-art systems.

The foregoing objects are met by apparatus and methods according to the present invention that are useful for detecting defects in a pattern defined by a mask, reticle, wafer, or other "sample." According to general aspects of the invention, such apparatus each comprise a charged-particle-beam optical system and a charged-particle detector. The charged-particle-beam optical system is adapted to scannably irradiate multiple charged particle beams simultaneously on respective measurement points ("loci") in an irradiation region on the surface of the sample. The charged-particle detector is situated so as to detect charged particles propagating, during irradiation, from the loci in the irradiated region of the sample. The charged-particle detector is also operable to produce data on whether or not the pattern in the irradiated region has any defects compared to a reference pattern.

Multiple example embodiments of this apparatus are disclosed. In certain embodiments, the charged-particle detector is situated so as to detect charged particles passing through the irradiated region of the sample. In other embodiments, the charged-particle detector is situated so as to detect secondary electrons (or reflected charged particles, or both) propagating from the loci in the irradiated region as a result of the charged-particle beams impinging on the loci.

An apparatus according to a first example embodiment comprises a source of multiple charged-particle beams (e.g., electron beams) directed toward the sample. The source is operable to generate a flux of charged particles propagating toward the sample. The charged-particle flux is preferably a collimated flux (e.g., by passage through a condenser lens) and passes through an aperture plate defining multiple apertures, thereby producing multiple parallel charged-particle beams propagating toward the sample. A first lens focuses each charged-particle beam on a separate locus in an irradiation region of the sample so as to produce secondary electrons upon impingement of the charged-particle beam on the locus. The apparatus also comprises a deflector (preferably located immediately downstream of the aperture plate) for simultaneously scanning each charged-particle beam within a limited area in the vicinity of the respective locus in the irradiation region. For each charged-particle beam, a detector is provided for detecting the secondary electrons released from the respective locus; thus, the detectors are located downstream of the sample. The secondary electrons are guided from each locus to the respective detector by a charged-particle lens. The charged-particle lens is preferably configured as a lens plate defining multiple apertures (each aperture functioning as an individual lens) that are situated so as to pass secondary electrons (or reflected charged particles, or both) produced from a respective locus.

In the first example embodiment, the charged-particle beams are preferably incident on the respective loci at oblique angles of incidence. I.e., the angles of incidence of each of the charged-particle beams on their respective loci is not zero (relative to a normal to the surface of the sample).

The first example embodiment also preferably comprises an electrode plate, which can be planar or curved. The electrode plate defines multiple apertures, wherein the secondary electrons generated at a particular locus are passed through a respective aperture in the electrode plate. The detectors are preferably situated downstream of the respective apertures in the electrode plate.

Further with respect to the first example embodiment, at least one detector is preferably situated on an axis satisfying a "specular reflection condition" with respect to the surface of the sample. Other detectors are displaced from respective axes representing specular reflection conditions for the corresponding loci.

A second example embodiment shares certain similarities with the first example embodiment. In the second example embodiment, the trajectory path of each of the charged-particle beams from the respective aperture in the aperture plate to the sample is preferably identical in length. According to one way in which this can be done, each of the apertures in the aperture plate has an axis, and the axes are individually tilted relative to the direction of propagation of the charged-particle beams from the aperture plate to the sample. According to another way in which this can be done, the entire aperture plate is tilted from an orientation perpendicularly transverse to the direction of propagation of the charged-particle beams.

A third example embodiment shares certain similarities with the first example embodiment except that, in the third example embodiment, the deflector for simultaneously scanning each charged-particle beam over its respective locus in the irradiation region is preferably located downstream of a charged-particle-beam lens that serves to make all the charged-particle beams parallel to each other before the beams impinge upon the respective loci on the sample.

The third example embodiment also preferably comprises a separate secondary electron deflector for the secondary electrons generated at each locus. The secondary electron deflectors are located downstream of the sample between the lens plate (of the secondary-electron lens) and the electrode plate. Each of the individual deflectors is energized in synchrony with scanning of each of the individual charged-particle beams over a respective region in the vicinity of the respective locus.

The third example embodiment can further comprise a control circuit operable to controllably energize the secondary-electron deflectors in synchrony with energization of the deflector for scanning the individual charged-particle beams. These features help direct the secondary electrons generated from each locus to the corresponding detector.

A fourth example embodiment shares certain similarities with the first and third example embodiments. I.e., similar to the first example embodiment, the scanning charged-particle-beam deflectors of the fourth example embodiment are located immediately downstream of the aperture plate. Also, similar to the third example embodiment, an individual secondary-electron deflector for the secondary electrons propagating from each locus is located downstream of the sample between the lens plate and the electrode plate in the fourth example embodiment.

In the fourth example embodiment, the lens plate of the secondary-electron lens preferably has a profile that is a portion of a first sphere. The electrode plate preferably has a profile that is a portion of a second sphere concentric with and having a radius greater than the first sphere. The arrangement of detectors has a profile that preferably is a portion of a third sphere concentric with the first and second spheres and having a radius greater than either of the first and second spheres. The secondary-electron lens plate is preferably made of a non-magnetic metal and during use is energized with a first potential. The electrode plate is charged during use with a second potential that is preferably greater than the first potential.

Further with respect to the fourth example embodiment, each of the lens apertures in the secondary-electron lens plate has an area and axis. The individual area of a lens aperture increases with an increase in the angle of the corresponding lens-aperture axis relative to a corresponding line indicating a normal specular reflective trajectory for the secondary electrons from a corresponding locus on the surface of the sample.

The fourth example embodiment also preferably comprises a shield situated between the secondary-electron lens plate and the secondary-electron deflectors. The shield preferably has a profile that is a portion of a fourth sphere concentric with the first, second, and third spheres. The fourth sphere has a radius that is greater than the radius of the first sphere but less than the radius of the second sphere. The shield is operable to shield the electrical fields produced by the secondary-electron deflectors.

Further with respect to the fourth example embodiment, the multiple charged particle beams collectively have a transverse profile in which the number of charged particle beams in a first dimension orthogonal to the direction of propagation is greater than the number of charged particle beams in a second dimension that is perpendicular to the first dimension and also transverse to the direction of propagation.

Any of the first through fourth example embodiments can further comprise a signal processor, a comparator, and a memory. The detectors are connected to the signal processor which is operable to receive electrical signals from the detectors based on secondary electrons received by the respective detectors. The comparator is connected to the signal processor and is operable to receive the processed signals from the detectors and compare them with reference signals so as to detect an error in the pattern defined by the sample at a particular locus. The memory is connected to the comparator and is operable to store reference signals and signals from the detectors until needed by the comparator.

A fifth example embodiment comprises a source of multiple charged particle beams (e.g., electron beams) directed toward the sample, a first lens, a charged-particle-beam deflector, an electrode plate, and multiple detectors. The first lens is situated so as to focus each particle beam on a separate respective locus in an irradiation region on a surface of the sample so as to produce secondary electrons upon impingement of the charged-particle beam on the locus. The deflector is situated so as to simultaneously scan each charged-particle beam over its respective locus in the irradiation region. The electrode plate defines multiple apertures, and is situated so as to attract the secondary electrons propagating from the irradiated region. Each aperture of the electrode plate is situated so as to receive secondary electrons (or reflected charged particles, or both) propagating from a corresponding locus in the irradiated region. A separate detector is provided for each charged-particle beam. Each detector is operable to receive secondary electrons released from the respective locus, and is situated downstream of the respective aperture in the electrode plate.

In the fifth example embodiment, the charged-particle beams preferably irradiate the sample at an oblique angle to the sample. As a result, space between individual detectors can be increased. Because each detector is disposed above an axis that satisfies the specular reflective conditions for the incident axis of the respective charged-particle beam relative to the sample surface, the efficiency with which secondary electrons are detected is improved.

In the fifth example embodiment, each of the apertures in the electrode plate defines a respective area. The area of the apertures preferably increases with an increase, for each aperture, in an angle between a line indicating a specular reflective condition for that aperture and an axis passing from the respective locus to the center of the respective aperture. As a result, each detector operates with equal efficiency without regard to detector position.

Further with respect to the fifth example embodiment, each charged-particle beam is deflected by the charged-particle-beam deflector so as to be incident to the respective detector even if the irradiation position of the charged-particle beam changes. This increase detection efficiency of secondary electrons.

The fifth example embodiment also preferably comprises a sub-stage deflector situated around or beneath the sample. The sub-stage deflector is operable to deflect the secondary electrons to the respective apertures in the electrode plate.

Also with respect to the fifth example embodiment, the electrode plate preferably has a profile that is a portion of a sphere.

A positive potential is applied to the electrode plate. The potential is higher than the positive potential of the sample surface. The trajectories of the secondary electrons discharged from the loci indicate that the secondary electrons are repelled by the sample surface which has an electrical field exhibiting a concave lens action. Secondary electrons discharged in different angular directions from identical loci are affected by the convex lens action imparted by the electrode plate. Thus, the secondary electrons accelerate, in the electric field created by the curved surface of the electrode plate, toward the electrode plate without much divergence. The detectors have an even higher positive potential than the electrode plate. As a result, the secondary electrons preferentially pass through the respective apertures in the electrode plate to the respective detector. Thus, the irradiation region of the sample is scanned simultaneously at multiple loci by the charged particle beams. This allows pattern-defect inspections to be conducted at high throughput. The detectors can be used to detect reflected charged particles (instead of secondary electrons) from the sample or both reflected charged particles and secondary electrons, the latter resulting in an improved S/N ratio.

As an alternative to a single electrode plate defining multiple apertures, multiple electrode plates each defining a single aperture can be used.

The center of the sphere, of which the electrode plate is a portion, is preferably located above the surface of the sample. This increases the concave lens effect whenever the potential of the electrode plate is higher than the potential of the surface of the sample. This, in turn, makes it easier to separate the secondary electrons and reflected charged particles from the loci.

The fifth example embodiment can also comprise a waveform shaper connected to each detector, a waveform comparator connected to each waveform shaper, a waveform generator connected to the waveform comparators, an error memory connected to the waveform comparators, and a main control system connected to the error memory and the waveform generator. The waveform shapers are operable to receive electrical signals from the respective detectors based on secondary electrons received by the respective detectors. The waveform shapers amplify the signals and shape the signals for downstream processing. The waveform comparators are operable to receive the processed signals from the respective waveform shapers and to compare them with a respective reference signal so as to detect an error in the sample pattern at the corresponding locus. If an error is detected, an error signal is produced. The waveform generator is operable to provide reference signals to the waveform comparators. The error memory is operable to store error signals from the waveform comparators corresponding to respective errors found at respective loci. The main control system is operable to process the error signals such as for display.

A sixth example embodiment comprises multiple charged-particle-beam sources. Each source generates multiple charged-particle beams (e.g., electron beams) directed toward the sample, and each source irradiates a respective irradiation region on a surface of the sample. A lens serves to focus each charged-particle beam on a respective locus in the respective irradiation region so as to produce secondary electrons (or reflected charged particles, or both) upon impingement of the charged-particle beam on the locus. A deflector serves to scan each charged-particle beam over its respective locus. For each source of charged-particle beams, an electrode plate is provided, situated so as to attract secondary electrons produced from the loci in the respective irradiation region. Each electrode plate defines multiple apertures. Each aperture is for the secondary electrons released from a respective locus in the respective irradiation region. A separate detector is situated downstream of each respective aperture in each electrode plate. The detectors serve to detect the secondary electrons released from the respective loci.

The sixth example embodiment can also comprise a waveform shaper connected to each detector, a waveform comparator connected to each waveform shaper, a waveform generator connected to the waveform comparators, an error memory connected to the waveform comparators, and a main control system connected to the error memory and the waveform generator. The waveform shapers are operable to receive electrical signals from the respective detectors based on secondary electrons (or reflected charged particles) received by the respective detectors. The waveform shapers amplify the signals and shape the signals for downstream processing. The waveform comparators are operable to receive the processed signals from the respective waveform shapers and to compare them with a respective reference signal so as to detect an error in the pattern at the corresponding locus. If an error is detected, an error signal is produced. The waveform generator is operable to provide reference signals to the waveform comparators. The error memory is operable to store error signals from the waveform comparators corresponding to respective errors found at respective loci. The main control system is operable to process the error signals such as for display.

As a result of using multiple electrode plates, each aperture in the electrode plates can be relatively large. This permits efficient collection and detection of substantially all the secondary electrons and reflected charged particles discharged from the sample, thereby improving the S/N ratio of the detection signals. This embodiment also exhibits higher throughput.

The surface of the sample in this and other example embodiments is scanned in two dimensions. Assuming the sample extends in the X and Y directions, each locus is scanned in the X-direction by the respective charged-particle beam. Scanning also progresses in the Y direction over a specified range by moving, for example, the sample in the Y direction during scanning of the charged-particle beams in the X direction. After scanning a defined region of the sample in the X and Y directions, the sample is "stepped" a defined amount in the X or Y direction and the X- and Y-direction scanning is repeated in an adjacent region. Such action is repeated until the entire sample has been scanned.

A seventh example embodiment comprises a source of a charged-particle-beam flux directed toward the sample. Downstream of the source is situated an aperture plate defining multiple apertures each for passing a portion of the charged-particle-beam flux so as to produce multiple charged-particle beams. Downstream of the aperture plate is situated a lens for focusing the charged-particle beams on respective loci in an irradiation region on the surface of the sample. Downstream of the lens is situated a deflector for simultaneously scanning each charged-particle beam over a limited area in the irradiation region corresponding to the respective locus. A scintillator plate is located downstream of the sample. The scintillator plate comprises multiple detection areas each corresponding to a respective locus. Each detection area is operable to produce photons in response to charged particles from the respective locus impinging on the detection area. A photoguide is situated downstream of each detection area on the scintillator plate for routing the photons to a terminus of the photoguide. A separate detector is situated at the terminus of each photoguide for receiving and detecting photons routed through the respective photoguide and for producing electrical signals in response to detecting the photons.

This example embodiment preferably also comprises a signal processor to which the detectors are connected. The signal processor is operable to compare the signals against corresponding reference signals and to thereby detect an error condition at any of the loci. This example embodiment also preferably comprises an error memory connected to the signal processor. The error memory is operable to store error signals from the signal processor corresponding to respective errors detected at respective loci.

The foregoing and additional features and advantages of the present invention will be more readily apparent from the following detailed description, which proceeds with reference to the accompanying drawings.

BRIEF DESCRIPTION OF THE DRAWINGS

FIGS. 2(a)–2(b) illustrate the production of secondary electrons discharged from a region on a sample irradiated with multiple charged particle beams, wherein FIG. 2(a) is an enlarged view of the irradiated region of the sample, and FIG. 2(b) is a transverse profile of the particle beams focused on the region of the sample.

FIG. 10 is an enlarged plan view showing regions of the sample that are scanned using the apparatus of FIG. 8 after a lateral shifting of the sample from its position in FIG. 9(b).

DETAILED DESCRIPTION

Example Embodiment 1

Figure 1:
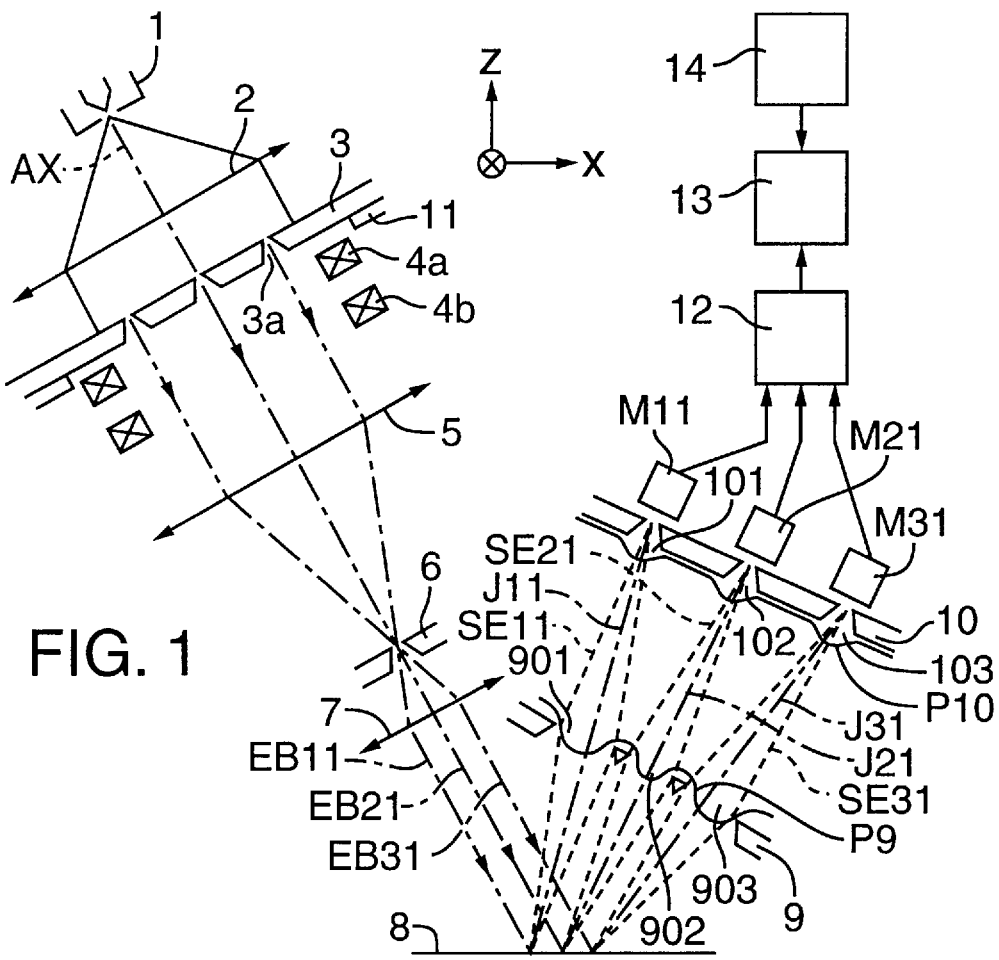
FIG. 1 is a schematic elevational view of a pattern-defect inspection apparatus according to Example Embodiment 1 of the invention.

This example embodiment of a pattern-defect inspection system is shown in FIG. 1. A charged-particle-beam flux (e.g., an electron-beam flux) is produced by a source 1 (e.g., an electron gun). A condenser lens 2 forms the charged-particle-beam flux into a flux parallel to the optical axis AX. The flux then irradiates an aperture plate 3 mounted on a retention base 11. The aperture plate 3 defines multiple apertures 3a. For example, the aperture plate 3 defines an array of multiple 1-$\mu$m diameter apertures at a pitch of 1 mm with six columns in the y-axis direction of the figure and three rows in the direction perpendicular to the y-axis. Thus, as charged particles pass through the aperture plate 3, eighteen irradiating charged-particle beams EB11 to EB36 are formed downstream of the aperture plate. (FIG. 1 only shows three charged-particle beams EB11, EB21, EB31 formed on the same plane as the page.) The following description is directed to these three beams, but it will be understood that what applies to any of the three beams EB11, EB21, EB31 applies to all of the charged-particle beams EB11–EB36.

The charged-particle beams EB11, EB21, ED31 are focused on a sample 8 by passage through a first lens 5, a stop 6, and a second lens 7. During passage from the aperture plate 3 to the first lens 5, the beams EB11, EB21, EB31 pass through first and second deflectors 4a, 4b that simultaneously deflect the beams EB11, EB21, EB31. The deflectors 4a, 4b cause the beams EB11, EB21, EB31 to raster-scan the sample 8.

Impingement of the charged-particle beams EB11, EB21, EB31 on the sample 8 generates respective secondary electrons SE11, SE21, SE31 discharged from the loci on the sample irradiated by the beams E11, E21, EB31. The secondary electrons SE11, SE21, SE31 pass through respective lens apertures 901, 902, 903 of a multiple-aperture lens 9. The secondary electrons SE11, SE21, SE31 then pass through respective apertures 101, 102, 103 defined in a multiple-aperture electrode plate 10. The secondary electrons SE11, SE21, SE31 are detected by respective detectors M11, M21, M31 (each preferably an electron-multiplier tube type of detector).

The lens 9 and the electrode plate 10 are each configured such that, for example, the irradiation point of the charged-particle beam EB11 on the sample 8, the center of the lens aperture 901, and the center of the aperture 101 are situated on a respective axis J11. In like manner, the lens aperture 902 and the aperture 102 are situated on a respective axis J21, and the lens aperture 903 and the aperture 103 are situated on a respective axis J31. In this embodiment, the lens 9 and the electrode plate 10 are planar normal to the axis J21, and are formed from a nonmagnetic metal, preferably aluminum or copper.

The charged-particle beams EB11, EB21, EB31 passing the respective apertures 101, 102, 103 impinge upon the respective detectors M11, M21, M31. Corresponding signals generated by the detectors M11, M21, M31 are processed by a signal processor 12; defects are detected by comparing, using a comparator 13, the signals from the detectors to reference signals relating to the pattern. Reference-signal data can be stored in a memory 14, associated with the comparator 13 and processor 12, for recall and use as needed.

Voltages $V_9$, $V_{10}$ (wherein $V_9 < V_{10}$) are applied to the multiple-aperture lens 9 and the multiple-aperture electrode plate 10, respectively. Furthermore, the potential of the lens 9 is set higher than the potential of the sample 8. The voltages $V_9$ and $V_{10}$ are adjusted so that the sample 8 and the lens apertures 901, 902, 903 form a conjugate relationship for secondary electrons with an energy of 2 eV. Equipotential surfaces for each of the lens 9 and the electrode plate 10 are designated by respective curves P9 and P10. The equipotential surfaces P9, P10 are situated close to the apertures of the lens 9 and electrode plate 10; both curves are convex on the sample side. Hence, the apertures 901, 902, 903 and the apertures 101, 102, 103 act as convex lenses for the secondary electrons. The surface area of each of the apertures is large to allow a large amount of secondary electrons to be collected in the detectors M11, M21, M31. However, because the apertures 901, 902, 903 function as convex lenses that converge the secondary electrons at the center of the respective apertures 101, 102, 103 as stated above, the surface area of each of the apertures 101, 102, 103 is small compared to the respective apertures 901, 902, 903.

As a result of the foregoing, secondary electrons discharged from the sample 8 can be efficiently detected by the detectors M11, M21, M31. Also, because the surface area of each of the apertures 101, 102, 103 is small and these apertures are separated from each other, the probability that a secondary electron SE21 generated by, for example, the beam EB21, will be incident to either of the detectors M11 or M31 is very small. This improves the signal-to-noise (S/N) ratio.

Figure 2A:
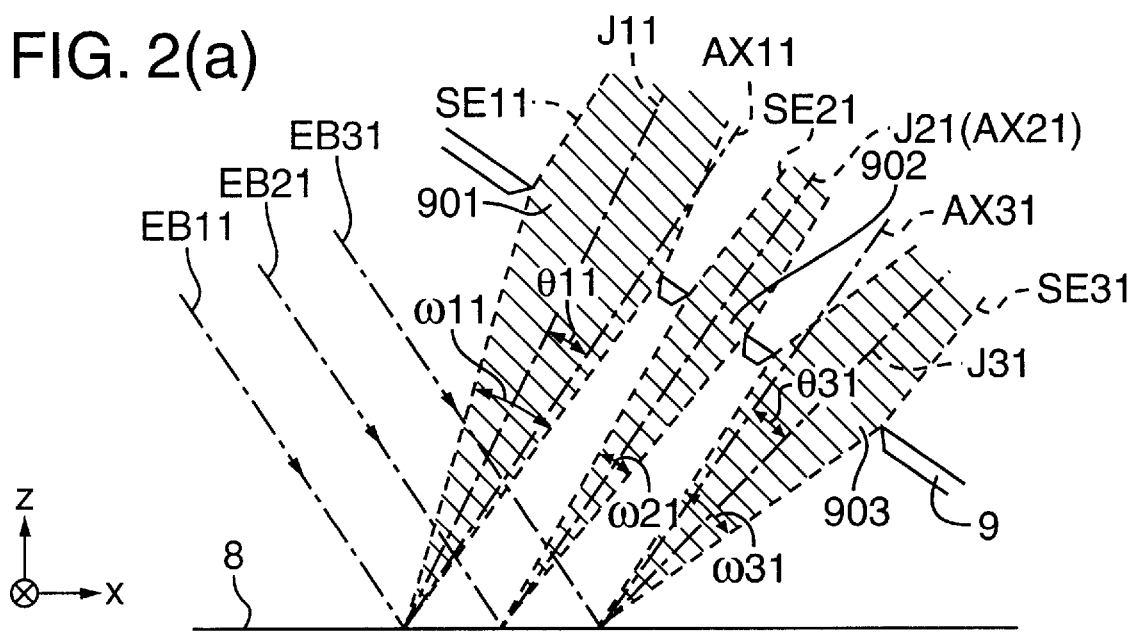

Furthermore, compared to the area of the aperture 902, the area of each of the apertures 901, 903 is larger. FIG. 2(a) more clearly depicts the differences in surface area of the apertures 901, 902, 903. (FIG. 2 is an enlarged view of the portion of FIG. 1 where the beams EB11, EB21, EB31 are incident to and reflect from the sample 8.)

Secondary electrons generated when the beams EB11, EB21, EB31 are irradiated onto the sample 8 are discharged following the "Cosine Law of Illumination." I.e., when the beams are irradiated perpendicularly onto the sample, the probability that secondary electrons will be discharged normal to the sample is highest; the probability decreases with increasing angle from the normal. If the angle from the normal with respect to the sample is designated θ and the solid angle extending from the center of an irradiation point on the sample is designated ω, then the amount of secondary electrons discharged in a given direction is proportional to ω cos θ. In this embodiment, because the beams EB11, EB21, EB31 are obliquely incident to the surface of the sample 8, there is a high probability of a secondary electron discharge in the direction of the axes respective axes AX11, AX21, AX31.

In FIG. 2(a), $\theta_{11}$ is an angle formed between the axes AX11 and J11, and $\theta_{31}$ is an angle formed between the axes AX31 and J31. The axes AX21 and J21 are coincident, so the angle $\theta_{21}$ is zero. Also, $\omega_{11}$, $\omega_{21}$, and $\omega_{31}$ are the solid angles of the apertures 901, 902, and 903, respectively. The ratio of the amount of secondary electrons incident to each aperture 901, 902, 903 is as follows:

$$\omega_{11} \cos \theta_{11} : \omega_{21} : \omega_{31} \cdot \cos \theta_{31} \qquad (1)$$

The solid angles $\omega_{11}$, $\omega_{31}$ of the lens apertures 901 and 903, respectively, are determined as follows:

$$\omega_{11} = \omega_{21}/\cos \theta_{11} \qquad (2)$$

$$\omega_{31} = \omega_{21}/\cos \theta_{31} \qquad (3)$$

According to the foregoing, the amounts of secondary electrons incident to the lens apertures 901 and 903, i.e., the amounts of secondary electrons incident to the detectors M11 and M31, are substantially equal to the amount of secondary electrons incident to the detector M21 disposed in the direction of reflection from the mirror surface, thereby improving the detection efficiency. Because the amount of secondary electrons incident to any of the apertures 901, 902, 903 is not dependent only on the angle θ, equations (2) and (3) are not limited for the solid angles $\omega_{11}$ and $\omega_{31}$.

If one were to irradiate the sample with charged-particle beams that impinge the sample from a direction perpendicular to the sample surface, with the intent of detecting secondary electrons, each detector would have to be situated in a direction inclined toward the irradiation points. Problems would arise with such a configuration because the space allotted for each detector would be very small, and the amount of secondary electrons that could be detected would also be small. However, when the charged-particle beams irradiate the sample obliquely, as in this embodiment, the space allotted for each detector is much larger. This allows more detectors to be disposed in addition to making it possible to install detectors in directions that satisfy specular reflection conditions. Therefore, this example embodiment provides a greater amount of detectable secondary electrons compared to when a charged-particle beam irradiates the sample from a normal direction. Thus, this embodiment exhibits a much improved S/N ratio and a higher scanning speed.

Figure 2B:
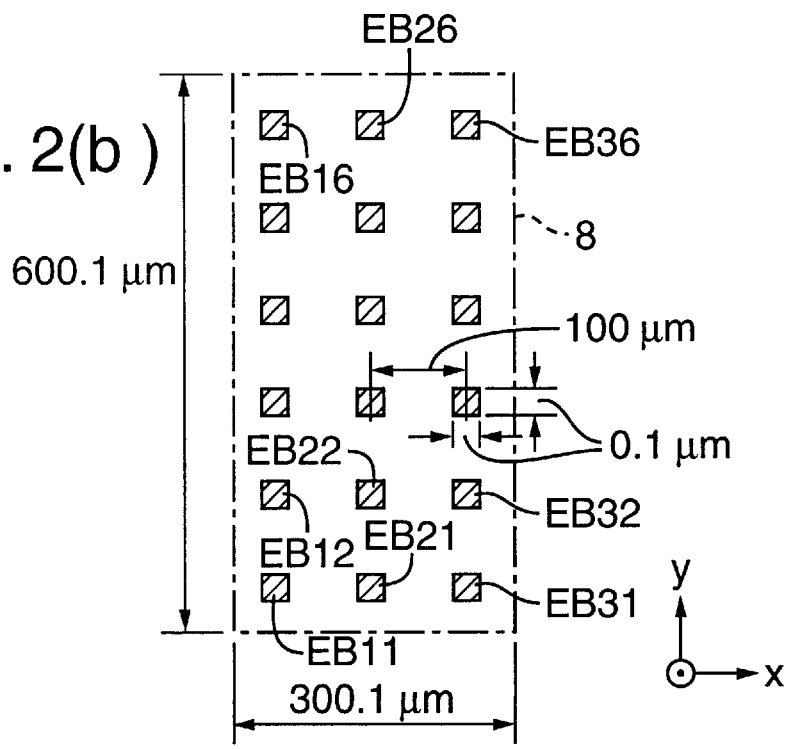

FIG. 2(b) shows impingement loci of 18 charged-particle beams EB11–EB36 focused on the sample 8. The figure shows the sample 8 as viewed from the second lens 7. If the reduction rate of the combination of lenses 5, 7 is 1/10, then the dimension of each beam EB11–EB36 as focused on the sample 8 is $(0.1 \mu m)^2$ at a pitch of 100 μm. Because the sample 8 is not perpendicular to the optical axis AX, each dimension in the direction of the x-axis is not precisely 0.1 μm and 100 μm, respectively. Nevertheless, in order to simplify this description, it is assumed that the dimensions are in fact $(0.1 \mu m)^2$ and 100 μm, respectively. If the deflection amount of each deflector 4a, 4b is 100 μm in each of the x- and y-directions over the sample 8, then a region on the sample 8 having a dimension of 300.1 μm×600.1 μm will be simultaneously scanned by the beam. After each region is scanned, the sample 8 moves in either the x-direction or the y-direction and is scanned again in like manner. By repeating this type of scan, the entire region of the sample 8 can be scanned. Because different regions of the sample 8 can be simultaneously scanned by the multiple charged-particle beams EB11–EB36, the scan time can be greatly reduced compared to a conventional apparatus in which scanning is performed using one beam.

Because a normal to the sample 8 slants toward the optical axis of each lens 5, 7, the beams EB11, EB31 at positions separated from the optical axis can be unfocused. Therefore, as shown in FIG. 2(b), the number of beams in the x-axis direction that change the distance between the second lens 7 and the sample 8 are less such that position-shifting in the z-direction is within the depth of focus. Moreover, although the beams EB11–EB31 are incident obliquely to the sample 8 in this embodiment, they can perpendicularly reflect incident as well. Excluding the benefits realized by the oblique incidence, other effects can be achieved. For example, the scan time can be reduced by using multiple charged-particle beams and by improving the S/N ratio by increasing the size of the lens apertures 901–903 around the peripheral portion.

Example Embodiment 2

Figure 3A:
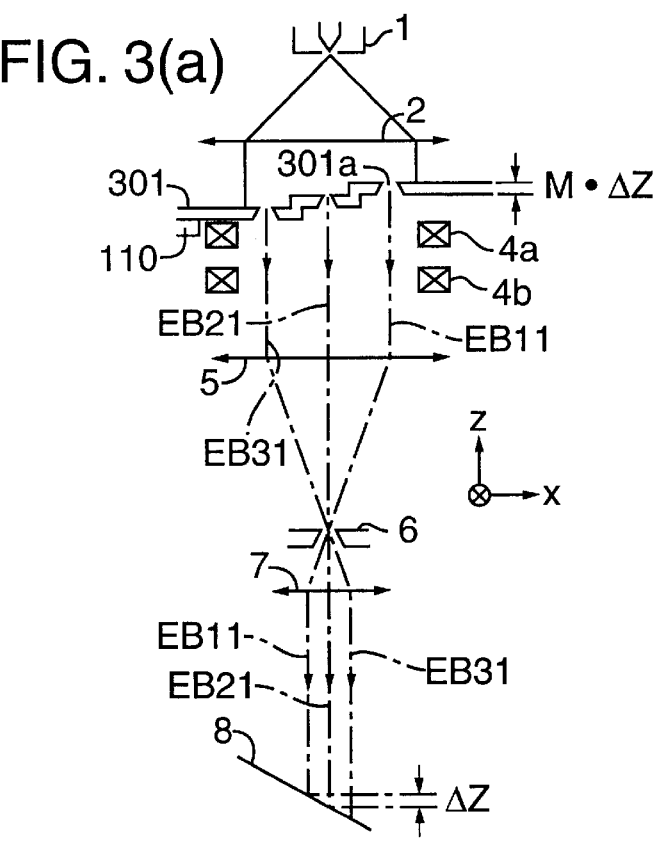
FIGS. 3(a)–3(b) are schematic elevational views of pattern-defect inspection apparatus according to Example Embodiment 2 of the invention, wherein the FIG.-3(b) configuration is a variant of the FIG. 3(a) configuration.
Figure 3B:
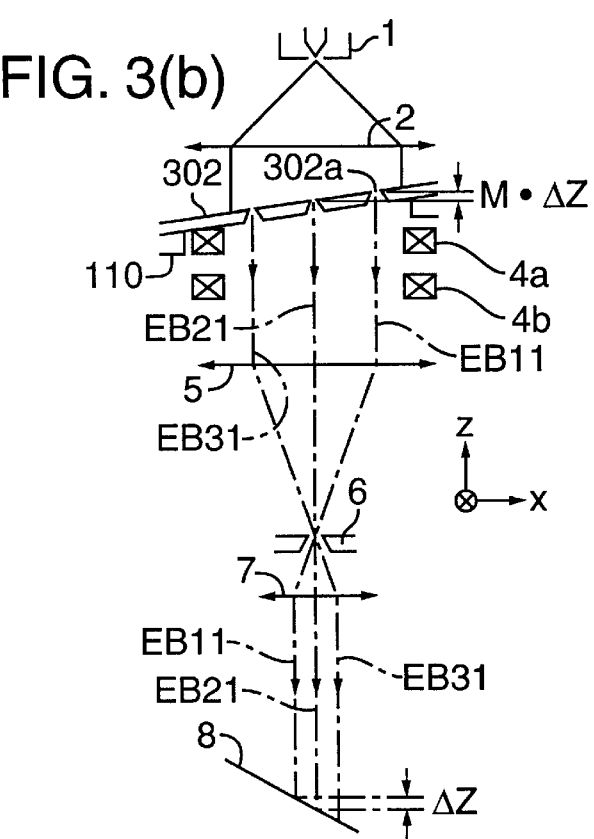

This example embodiment is depicted in FIGS. 3(a)–3(b). In FIGS. 3(a)–3(b), components that are the same as in FIG. 1 have the same reference designators and are not described further. The secondary electron detection system (e.g., multiple-aperture lens 9 and detectors M11–M31) in this example embodiment is the same as in the first example embodiment and is not shown in FIGS. 3(a)–3(b). As in the first example embodiment, the charged-particle beams EB11, EB21, EB31 obliquely irradiate the surface of the sample 8. As a result, the distance from the second lens 7 to the irradiation points of the sample 8 differs for each beam.

Therefore, in the second example embodiment, the distance of the object side can be set to correspond to the distance of the image side, namely, the distance from the first lens 5 to the aperture 301a of the multiple-aperture plate 301. As a result, the length of the irradiation path from the aperture 301a to the surface of the sample 8 is equal for all the charged-particle beams. The multiple-aperture plate 301 of FIG. 3(a) is configured such that the length of the irradiation path is made equal by providing each aperture 301a of the plate with a step profile as shown in the figure. In contrast, the multiple-aperture plate 302 of FIG. 3(b) is configured such that the lengths of the irradiation paths are made equal by the tilting the retaining base 110 (with the planar multiple-aperture plate 302 attached thereto) at an angle to the first lens 5. In view of such a tilt, if it is desired that the charged-particle beam on the sample 8 be circular, the aperture 302a on the plate 302 can have an elliptical shape.

As shown in FIG. 3(a), if the reduction ratio of the first and second lenses 5, 7, respectively, is 1/M whenever the difference in the distance from the second lens 7 to the sample 8 is ΔZ in relation to the charged-particle beams EB11 and EB31, then the elevational difference from the aperture forming the charged-particle beam EB11 to the aperture forming the charged-particle beam EB21 is MΔZ. In other words, if only the distance ΔZ from the second lens 7 to the sample 8 is made larger, then only the distance MΔZ from the first lens 5 to the aperture 301 becomes smaller.

Thus, the focus conditions for all the charged-particle beams can be satisfied by changing the distance in the direction of the z-axis of the aperture 301a in response to slanting of the sample 8 as well as making it possible to keep the beam over the sample 8 from becoming unfocused. Furthermore, as shown in FIG. 2(b), because there is a larger number of charged-particle beams in the direction of the y-axis compared to the direction of the x-axis, it is easy for image-surface warping of the lens system to occur. However, by shifting the position of the aperture in the direction of the z-axis, this can be corrected.

Example Embodiment 3

Figure 4:
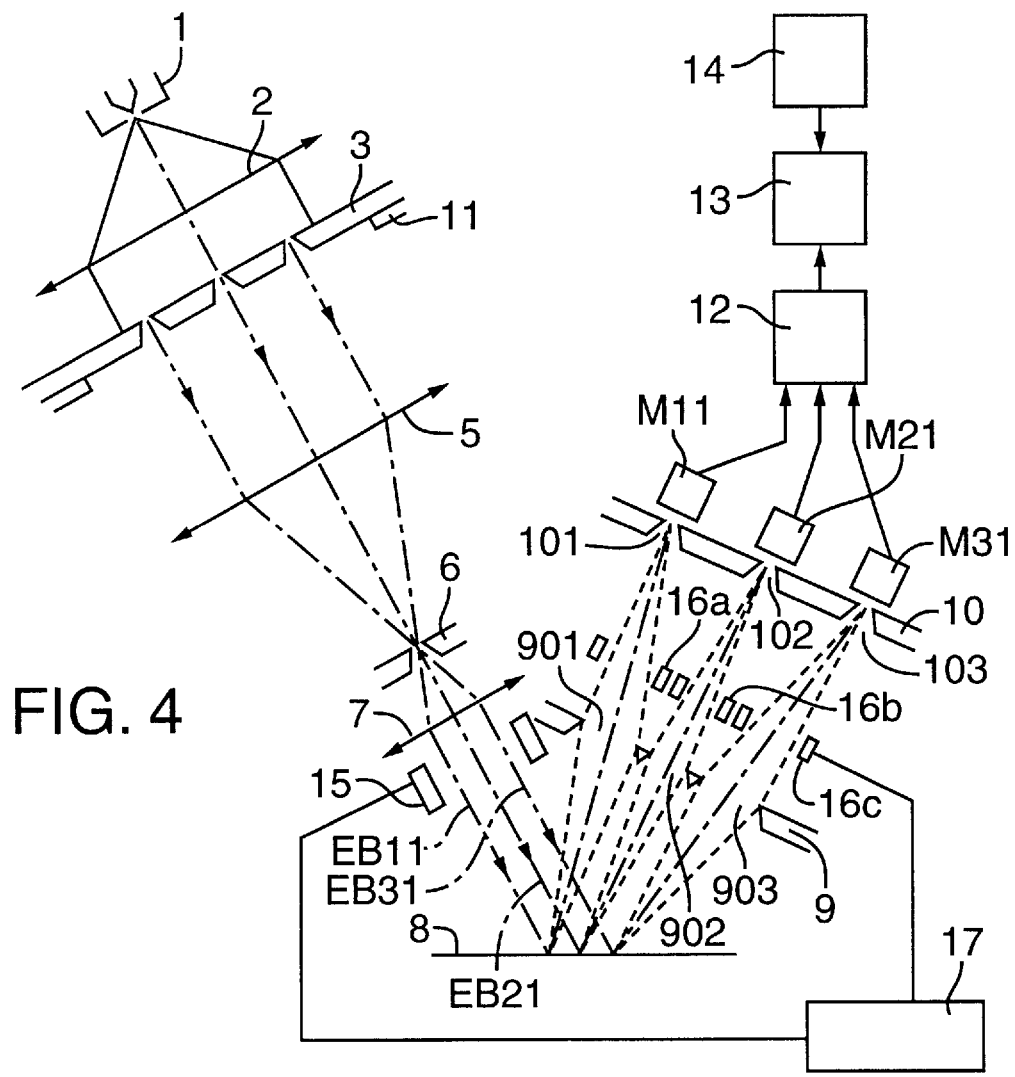
FIG. 4 is a schematic elevational view of a pattern-defect inspection apparatus according to Example Embodiment 3 of the invention.

This example embodiment is shown in FIG. 4, in which components that are the same as in FIG. 1 are identified using the same reference designators and are not described further.

In the system depicted in FIG. 1, the first and second deflectors 4a, 4b were disposed between the multiple-aperture plate 3 and the first lens 5 for scanning the charged-particle beams EB11–EB31. The system depicted in FIG. 4 does not employ the deflectors 4a, 4b. Rather, a single deflector 15 is disposed between the multiple-aperture plate 3 and the sample 8. In addition, each flux of secondary electrons passing through respective apertures 901, 902, 903 has associated therewith an individual deflector 16a–16c, respectively. A control circuit 17 controls operation of the deflectors 15 and 16a–16c.

When the deflector 15 scannably deflects the beams EB11–EB31, the respective positions on the sample 8 at which the beams are incident changes. I.e., locations on the sample from which the secondary electrons arise change. As a result, secondary electrons passing through the apertures 901 and 903 are shifted from the centers of the respective apertures of the multiple-aperture plate 10. This also causes a change in detection efficiency by the detectors M11–M31. Hence, in this example embodiment, the secondary electrons SE11–SE31 deflect by passage through the respective deflector 16a–16c in synchrony with the scanning of the deflector 15. Secondary electrons that pass through the apertures 901 and 903 are controlled such that they are incident at the center of the respective aperture of the multiple-aperture plate 10. This allows any changes in detection efficiency to be reduced even when the charged-particle beams are scanned.

For example, at a time when the voltage applied to the deflector 15 is 0 V, the voltage applied to the deflectors 16a–16c that causes the respective detectors M11 to M31 to exert maximum deflection is stored in the memory 14. Also, voltages applied to the deflectors 16a–16c that result in maximal output from the detectors M11, M21, M31 are determined and stored in the memory 14 for both positive and negative voltages applied to the deflector 15 to effect scanning of the charged-particle beam. Based on such stored data, the voltages applied to the deflectors 16 are controlled relative to the voltage applied to the deflector 15.

Example Embodiment 4

Figure 5:
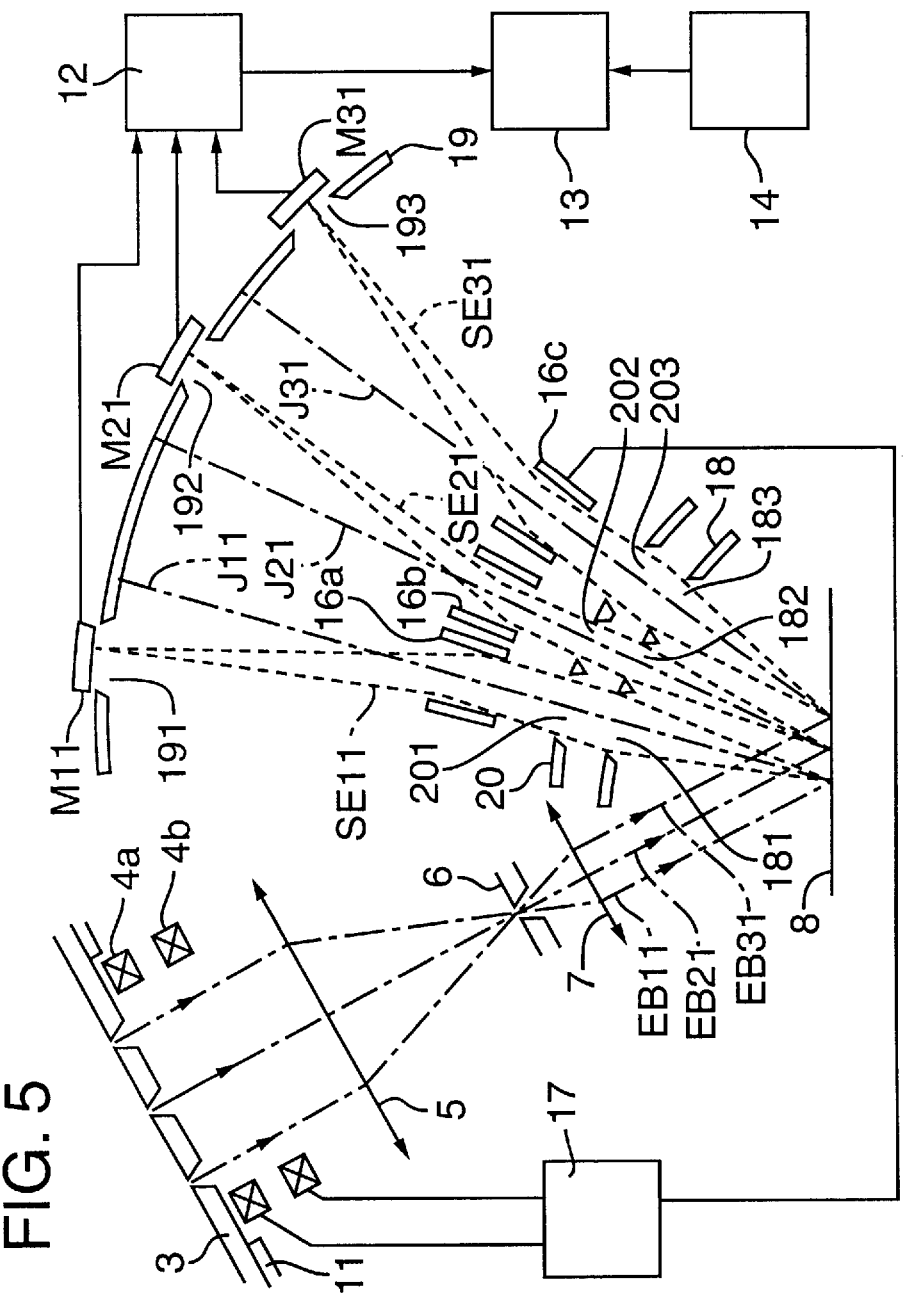
FIG. 5 is a schematic elevational view of a pattern-defect inspection apparatus according to Example Embodiment 4 of the invention.

This example embodiment is depicted in FIG. 5. Components in FIG. 5 that are the same as in FIG. 1 have the same reference designators and are not described further. The embodiment shown in FIG. 5 comprises a multiple-aperture lens 18 defining lens apertures 181, 182, 183, and a multiple-aperture plate 19 defining apertures 191, 192, 193. The lens 18 and plate 19 respectively correspond to the multiple-aperture lens 9 and the multiple-aperture plate 10 of FIG. 1.

In the FIG.-1 embodiment, the multiple-aperture lens 9 and the multiple-aperture plate 10 are planar members disposed upstream of the planar surfaces of the detectors M11 to M31. In the FIG.-5 embodiment, in contrast, the multiple-aperture lens 18 and the multiple-aperture plate 19 each define a portion of a sphere, wherein the radius of the sphere for the multiple-aperture plate 19 is greater than the radius of the spherical shell for the multiple-aperture lens 18. The center of each spherical shell is the point of incidence of the beam EB21 on the surface of the sample 8. The detectors M11, M21, M31 are also situated on a sphere (having a slightly greater radius than the sphere of the multiple-aperture plate 19) also centered on the point of incidence of the beam EB21 on the surface of the sample 8.

As can be seen in FIG. 5, the apertures 191, 192, 193 of the multiple-aperture plate 19 are formed at positions shifted away from the axes J11, J21, J31, respectively. The beams EB11, EB21, EB31 passing through the apertures 181, 182, 183, respectively, are incident at the center of the respective apertures 191, 192, 193 as a result of being deflected by each deflector 16a, 16b, 16c, respectively.

Because the apertures 901, 902, 903 are disposed over a planar surface in the system of FIGS. 1 and 2, the aperture 901 is situated a longer distance from the sample 8 than the aperture 903. As a result, the transverse area of the aperture 901 is greater than the transverse area of the aperture 903. In the system of FIG. 5, in contrast, because the apertures 181, 182, 183 are situated over a spherical surface centered on the point of incidence of the beam EB21 on the surface of the sample 8, the transverse area of each of the apertures 181 and 183 are almost equal.

A shield 20 is provided between the multiple lens 18 and the deflector 16. Apertures 201, 202, and 203 are formed on the shield 20 for the purpose of passing the secondary electrons SE11, SE21, and SE31.

Further with respect to FIG. 5, a shield. 20, made of a non-magnetic metal, is situated concentrically to the multiple-aperture lens 18 and the multiple-aperture plate 19. I.e., the shield 20 represents a portion of a sphere having a center at the point of incidence of the beam EB21 on the surface of the sample 8. The shield 20 shields the electric field of the deflectors 16a–16c from influencing performance of the multiple-aperture lens 18.

Because the multiple-aperture lens 18 and the multiple-aperture plate 19 are preferably concentric, the equipotential surface of the electric field formed between the multiple-aperture lens 18 and the multiple-aperture plate 19 is also concentrically spherical. As a result, aberrations arising from the electric field do not occur, which allows secondary electrons to be efficiently detected. Also, because the secondary electrons SE11, SE21, SE31 are perpendicularly incident to the apertures 181, 182, 183 of the multiple-aperture lens 18, aberrations arising from the multiple-aperture lens 18 can be better controlled. Additionally, since the electric field of the deflectors 16i a, 16b, 16c is shielded by the shield 20, any influence on the electric field of the apertures 181, 182, 183 can be eliminated. This also facilitates reduction of aberrations in the multiple-aperture lens 18.

During inspection of pattern defects in a sample, there are instances in which secondary electrons can be detected favorably and there are instances in which reflected electrons or charged particles of the beams irradiating the sample can be detected favorably. In the embodiment of FIG. 5, because the apertures 191, 192, 193 are shifted away from the axes J11, J21, J31, respectively, reflected electrons and/or reflected charged particles having low deflection sensitivity are not incident to the apertures 191, 192, 193, respectively, even though the secondary electrons SE11, SE21, SE31 are directed to the center of the respective apertures 191, 192, 193 by the deflectors 16a, 16b, 16c, respectively. In other words, when detecting secondary electrons, reflected electrons or charged particles are not detected. When detecting reflected electrons or charged particles, in contrast, the voltages applied to the deflectors 16a, 16b, 16c can be adjusted to ensure that the reflected electrons or charged particles are incident to the apertures 191, 192, 193.

Although the foregoing description was directed, by way of example, to the beams EB1, EB21, EB31, the same description also applies to all the other beams EB12 to EB36. Moreover, it is to be understood that the general principles described above are equally applicable whether or not the charged-particle beams are electron beams or other charged-particle beam (such as an ion beam).

Therefore, because different regions on a sample can be simultaneously inspected by multiple charged-particle beams, inspection time can be greatly reduced without losing inspection accuracy.

Example Embodiment 5

Figure 6:
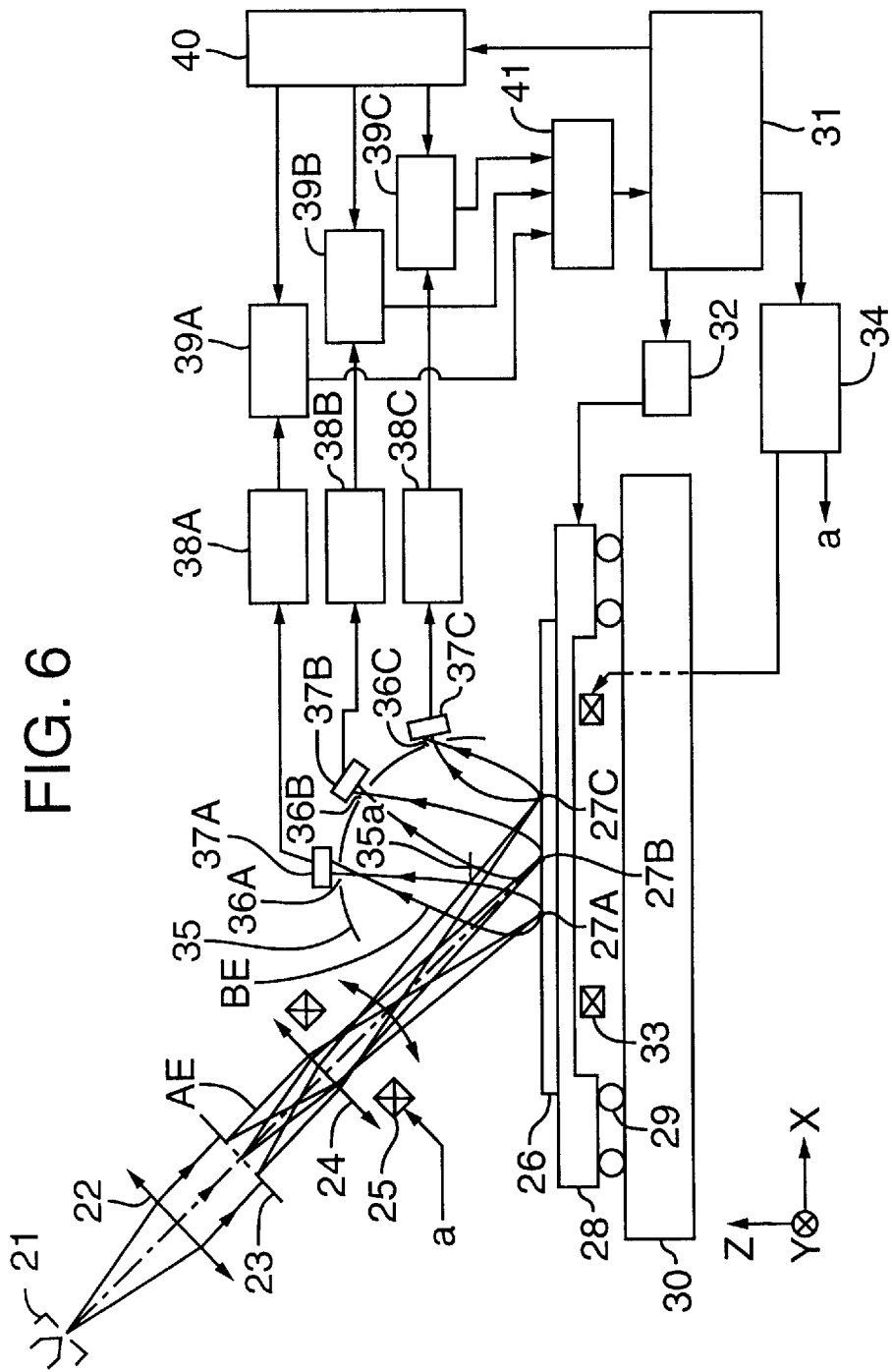
FIG. 6 is a schematic elevational view of a pattern-defect inspection apparatus according to Example Embodiment 5 of the invention.

This example embodiment is illustrated in FIG. 6. This embodiment utilizes multiple charged-particle beams. Because this embodiment has certain characteristics of a scanning electron microscope (SEM) provided with multiple beams, the embodiment is referred to herein as a "multiple channel SEM". In FIG. 6, the Z-axis is parallel to the normal of the surface of a sample 26, the X-axis extends parallel to the plane of the page of FIG. 6 and perpendicular to the Z-axis, and the Y-axis is perpendicular to both the Z-axis and the X-axis.

A flux of charged particles is discharged from a suitable source (e.g., an electron gun) 21 and passes through a condenser lens 22. The flux is incident to a multiple-aperture plate 23 defining multiple apertures (e.g., nine apertures in a 3×3 arrangement). As the flux passes through the aperture plate 23, multiple charged-particle beams AE are produced each originating from a respective aperture and each comprising a stream of "primary particles". The charged-particle beams AE pass through a "projection lens" 24 and are incident to the surface of the sample 26. The surface of the sample 26 and the surface of the aperture plate 23 are substantially conjugate with respect to the projection lens 24, and the beams AE are converged on the multiple incidence points (also termed "measurement points", e.g., nine points in a 3×3 arrangement) on the surface of the sample 26.

In FIG. 6, only three measurement points 27A, 27B, 27C are shown, but it will be understood that the three measurement points shown are representative of all the measurement points. A scanning deflector 25 disposed between the projection lens 24 and the sample 26 scans the beams AE over the sample 26. A main control system 31, which exercises supervisory control over the entire operation of the system of FIG. 6, controls the amount of deflection imparted by the scanning deflector 25 by regulating the output of a deflector driver 34.

Figure 7:
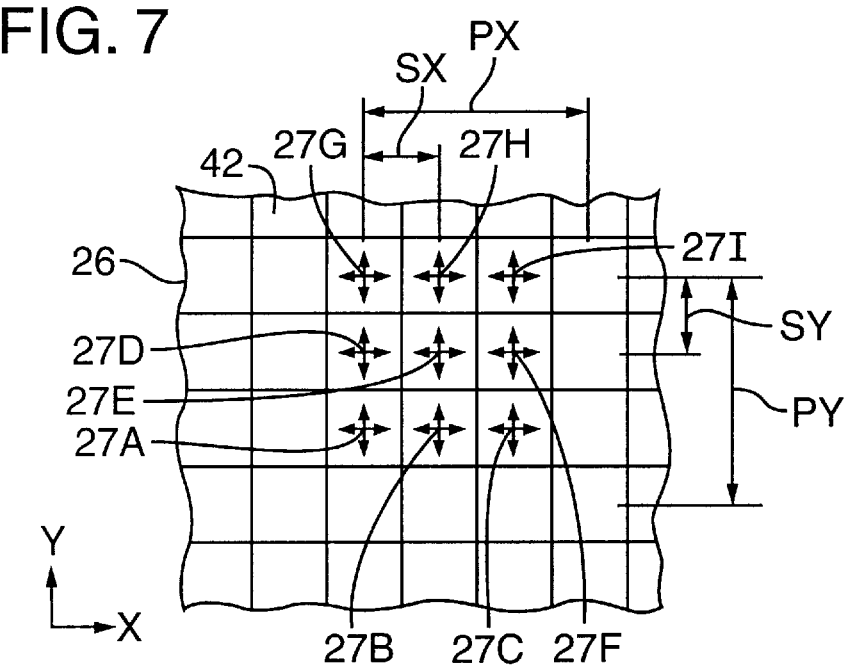
FIG. 7 is an enlarged plan view showing the manner in which the measurement points on the sample are scanned by the apparatus of FIG. 6.

FIG. 7 shows the nine measurement points 27A–27I on the sample 26. The measurement points 27A–27I are arranged in 3 lines×3 columns at a pitch SX in the X-direction and a pitch SY in the Y-direction. As an example, pitch SX and pitch SY are each approximately 1 mm. Patterns are formed on the sample 26 at a period pitch PX=3(SX) in the X-direction and a period pitch PY=3(SY) in the Y-direction. Therefore, the orientation pitch of the measurement points 27A–27I according to the primary particles on the sample 26 is (PX)/3 or (PY)/3 on the sample 26. In addition, the measurement points 27A–27I are arranged such that regions on the sample surface extending over the area SX×SY are two-dimensionally scanned by the scanning deflector 25. Secondary electrons are generated from each measurement point 27A–27I.

Referring further to FIG. 6, the sample 26 is mounted to a movable stage 28. The stage 28 is mounted on a stage drive 29 mounted on a base 30. The stage drive 29 can comprise, for example, a feed screw and a drive motor (not shown). The stage drive 29 moves the stage 28 incrementally in the X- and Y-directions. The position of the stage 28 is monitored by a laser interferometer (not shown, but as known in the art). Data from the laser interferometer is supplied to the main control system 31. The main control system 31 controls operation of the stage drive 29 by regulating the output of a stage driver 32.

A sub-stage deflector 33 is situated proximally to the sample 26 beneath the stage 28 above the base 30. The sub-stage deflector 33 two-dimensionally deflects secondary electrons (or reflected charged particles, or both) released from the sample 26. The main control system 31 controls the amount of deflection imparted by the deflector 33 by regulating the output of the deflector driver 34.

An electrode 35 with a spherically curved conductor surface is situated above the sample 26. The concave surface of the electrode 35 is oriented toward the sample 26. By way of example, the concave surface of the electrode has a spherical radius of 4 mm. The center 35a of such a spherical concave surface is 2 mm above the surface of the sample 26.

Normally, the electrical potential of the sample 26 is 0 volts (i.e., "ground"). A positive (+) voltage of 1000 V is applied to the electrode 35. The electrode 35 defines nine apertures 36A–36I corresponding to the nine measurement points 27A–27I, respectively, on the sample 26. Immediately downstream of the apertures 36A–36I are secondary electron detectors 37A–37I arranged so as to detect secondary electrons passing through the apertures 36A–36I. (In FIG. 6, only three apertures 16A–16C corresponding to the three measurement points 27A–27C on the sample 26 and three corresponding secondary electron detectors 37A–37C are elect. Although the three secondary electron detectors 37A–37C are described, the other six secondary electron detectors 37D–37I are identical.)

In this example embodiment, each secondary electron detector 37A–37I is preferably a micro-channel plate energized with, for example, a positive (+) voltage of 10 kV. Alternatively, for example, a plastic scintillator can also be used for each secondary electron detector 37A–37I.

The detection signal produced by each secondary electron detector 37A–37C is amplified and converted to a binary signal by a respective waveform shaper 38A–38C. The binary signals are routed to the inputs of respective waveform comparators 39A–39I. The main control system 31 provides, to a waveform generator 40, design data concerning the circuit pattern on the sample 26 currently positioned at the measurement points 27A–27I. The waveform generator 40 provides a binary reference signal corresponding to the circuit pattern on the sample 26 and supplies the binary signal to inputs of the waveform comparators 39A–39I. The waveform comparators 39A to 39C compare each detection signal with a reference signal. At any of the measurement points 27A–27I, whenever the detection signal and the reference signal differ by more than a specified amount, a logic "high" ("1") signal is produced by the respective waveform comparator 39A–39I. All other measurement points initiate production of a logic "low" ("0") signal indicating "error". Each such error signal is supplied to an error memory 41. The error memory 41 stores the error signals for respective measurement points 27A–27I on the sample 26. The main control system 31 reads the error signals from the error memory 41. Whenever there is a region with an error signal at a high level of "1", namely, when there is a defect in a portion of the circuit pattern defined by the sample 26, the main control system 31 determines the location of the defect and displays the detected defect via a suitable display (not shown).

Inspection of defects in the sample 26 is performed as follows. The main control system 31 drives the stage 28, thereby moving a first inspection region on the sample 26 into position for impingement by the primary particles AE. The scanning deflector 5 causes the beams of primary particles to scannably move as indicated by the arrows in FIG. 7. Each measurement point 27A–27I (at which the primary particles are converged) is scanned two-dimensionally in parallel within a region of dimensions SX×SY adjacent to the sample 6. In synchrony with scanning the primary particles, the main control system 31 operates the sub-stage deflector 33 which causes secondary electrons (or reflected charged particles, or both) released from the measurement points 27A–27I on the sample to propagate toward the respective apertures 36A–36I in the electrode 35. Because the energy of the secondary electrons is small compared to the primary particles, the secondary electrons can be rather easily deflected toward the corresponding aperture 36A–36I by the deflector 33 located below the stage 38. The main control system 31 also provides reference data to the waveform generator 40 concerning the portion of the pattern currently positioned at the measurement points 27A–27I.

In FIG. 6, the secondary electrons BE discharged from the nine measurement points 27A–27I (only the points 27A–27C are shown) on the sample 26 are accelerated by the electrode 35 (having a positive potential for secondary electrons) toward the respective aperture 36A–36I. Since the center 35a of the reference surface of the electrode 35 is situated above the surface of the sample 36, secondary electrons from each measurement point 27A–27I are directed toward the corresponding aperture 36A–36I by a concave lens effect of the electrode 35 along a repelling trajectory.

A computer simulation can be employed in advance to calculate the best positions on the spherical surface inside the electrode 35 for providing the apertures 36A–36I. By a further convex lens action contributed by a positive voltage applied to the electrode of each of the secondary electron detectors 37A–37I, most of the secondary electrons BE reaching the respective apertures 36A–36I pass through the apertures and are captured by the respective secondary electron detectors 37A–37I. Even if the positions of the measurement points 27A–27I change under the influence of the scanning deflector 25, the deflector 33 deflects the secondary electrons BE such that any such change is effectively canceled. Thus, the secondary electrons produced at the measurement points 27A–27I are incident to the corresponding secondary electron detector 37A–37I.

Detection signals produced by the secondary electron detectors 37A–37I are supplied to the respective waveform comparators 39A–39I via the respective waveform shapers 38A–38I. As a result of comparisons, by the waveform comparators 39A–39I, of the detection signals to corresponding reference signals supplied by the waveform generator 40, error signals are created. These error signals are supplied to the error memory 41.

In FIG. 7, after completion of the scan of each measurement point 27A–27I, the sample 26 is moved ("stepped") the distance PX in the X-direction and/or the distance PY in the Y-direction. Stepping is effected by the main control system 31 driving the stage 28 via the stage drive 29. After each "step," a scan of each measurement point 27A–27I is executed as described above, and the error signals are stored in the error memory 41. Such stepping and scanning are repeated until the entire sample has been scanned. The main control system 31 then reads the error signals from the error memory 41 corresponding to each step of the sample 26. At each step, the locations on the sample 26 where errors were detected are shown on an appropriate display (not shown in figure).

In FIGS. 6 and 7 described above, nine measurement points 27A–27I ("loci") on the sample surface are simultaneously scanned. Hence, compared to a conventional sample-inspection apparatus with which the sample is scanned at one only one measurement point at a time, sample-scanning time is greatly reduced with this example embodiment, with a corresponding increase in throughput of the inspection process.

Further with respect to FIG. 7, the measurement points 27A–27I of this example embodiment are arranged on the sample 26 at a pitch PX and PY, wherein the pitches SX and SY are (PX)/3 and (PY)/3, respectively. Therefore, when one scan is completed and the sample 26 is stepped by a distance PX in the X-direction or PY in the Y-direction, the reference signal supplied from the waveform generator 40 to the waveform comparators 39A–39I for the new scan can be the same as the reference signal supplied during the previous scan. With such a scheme, creation of a suitable reference signal is simple, thereby enabling the control sequence during pattern-defect inspection to be simplified.

Although the orientation pitch SX, SY of the measurement points 27A–27I are (PX)/3 and (PY)/3, respectively, the orientation of the pitch SX, SY can be set to the pitch of the periodic circuit pattern on the sample itself or to a suitable integral multiple of this pitch. Therefore, because circuit patterns identical to each other typically serve as the inspection targets at the measurement points 27A–27I, the waveform generator 40 can supply identical reference signals to the signal comparators 39A–39I. This allows the waveform generator 40 to be simplified in addition to simplifying the control sequence during the pattern-defect inspection. However, when the pitch of the periodic circuit pattern on the wafer 6 is large, the orientation pitch SX, SY of each of the measurement points 27A–27I can be set to 1/n ("n" is a positive integer) value of the respective pitch PX, PY of the particular periodic circuit pattern.

By providing a charged-particle-beam scanning system that scans charged-particle beams irradiated from an irradiation source onto a sample, and a deflection system that deflects secondary electrons (or reflected charged particles) discharged from the sample toward an electrode in synchrony with the charged-particle-beam scanning system, the charged-particle beams can be electrically scanned at a high speed, thereby improving the inspection speed.

Because the secondary electrons (or reflected charged particles, or both) from each measurement point are precisely guided to the corresponding apertures in the electrode plate even while scanning the charged-particle beams, inspection of the sample can be performed with high precision.

The electrode plate is preferably configured as a portion of a sphere having a center located above the surface of the sample. As a result, a concave lens action is enhanced by applying a positive (+) potential to the electrode plate. Even if multiple apertures are defined by the electrode plate, the secondary electrons (or reflected charged particles, or both) from the measurement points corresponding to the apertures are incident to the respective detectors without substantial "mixing".

By energizing the electrode plate at a higher potential than the potential of the sample, the secondary electrons (or reflected charged particles, or both) from the sample are efficiently incident to the electrode plate.

By providing a scanning system that mechanically scans the sample relative to the irradiation system, for example, it is possible to inspect a wide inspection region one time over the sample by means of combining an electronic scan and a mechanical scan.

When the sample defines a fixed circuit pattern that is repeated many times at a particular pitch, when the pitch of the charged-particle beams irradiated from the irradiation system onto the sample is set to 1/n (wherein "n" is a positive integer), the same reference signal can be used for each detector. This allows substantial simplification of either the control sequence during inspection of the sample or of the inspection control circuitry.

Example Embodiment 6

Figure 8:
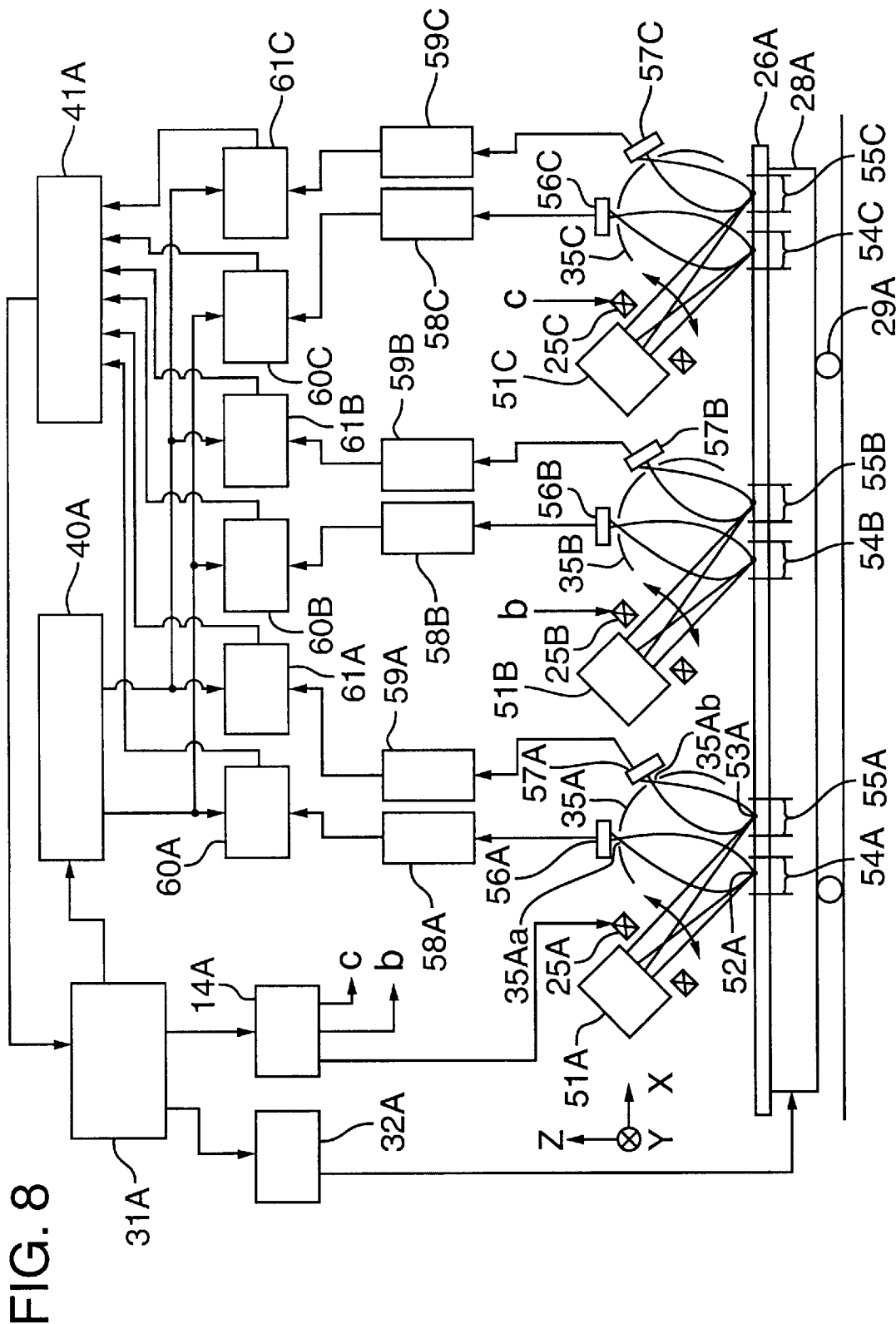
FIG. 8 is a schematic elevational view of a pattern-defect inspection apparatus according to Example Embodiment 6 of the invention.

This example embodiment is shown in FIGS. 8–10. This example embodiment, configured as a "multiple-channel SEM," utilizes multiple charged-particle beams and combines an electronic scan with a mechanical scan to increase throughput. This example embodiment has many features that are similar to those in example embodiment 5.

In the FIG.-8 embodiment, by way of example, three charged-particle-beam irradiation systems 51A, 51B, 51C are utilized. Each irradiation system 51A–51C comprises a particle-beam source, condenser lens, aperture plate, and projection lens similar to the FIG.-5 embodiment. Each irradiation system 51A–51C has associated therewith a spherical electrode 35A–35C, respectively to which is applied a potential of approximately 1000 V. A scanning deflector 25A, 25B, 25C is disposed between the respective irradiation system 51A–51C and the sample 26A.

Figure 9A:
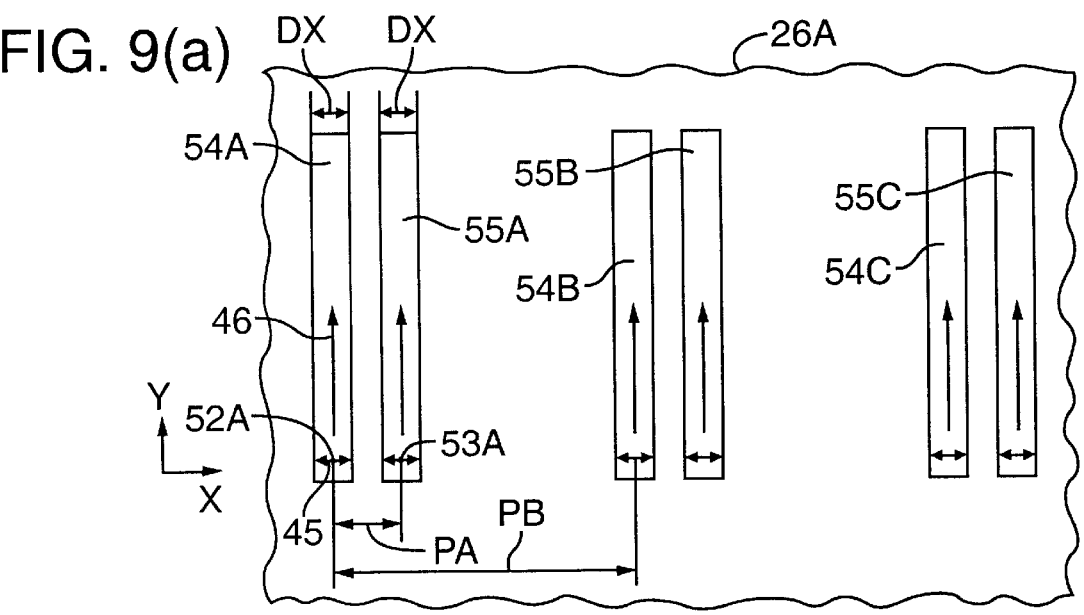
FIG. 9(a) is an enlarged plan view showing first regions of the sample that are scanned using the apparatus of FIG. 8.
Figure 9B:
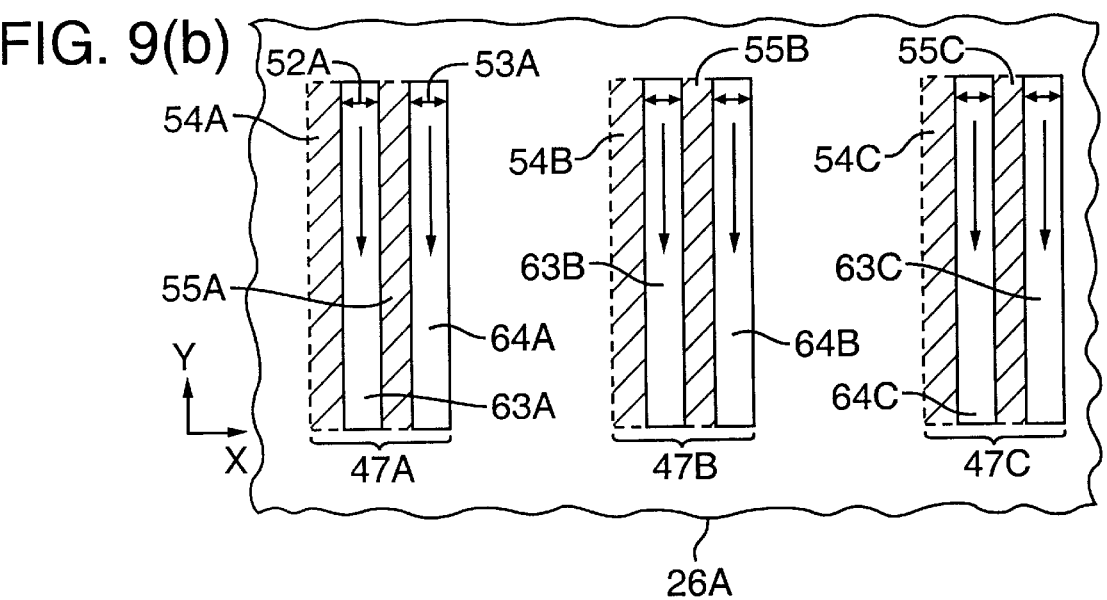
FIG. 9(b) is an enlarged plan view showing second regions of the sample that are scanned using the apparatus of FIG. 8 after a lateral shifting of the sample from its position in FIG. 9(a).

As shown in FIG. 9(b), the pitch PB is in the X-direction, and, by way of example is approximately 10 mm.

The irradiation system 51A, as an example of the irradiation systems 51A–51C, produces two finely drawn primary charged-particle beams that are irradiated onto respective measurement points 52A, 53A separated by a gap PA (FIG. 4(a)) in the X-direction on the sample 26A. The scanning deflector 25A scans the beams in the X-direction relative to the measurement points 52A, 53A within scanning regions 54A, 55A each having a width DX. If, for example, the gap PA between the measurement points 52A, 53A is 2 mm, then the width DX of the scanning regions 54A, 55A is set to approximately 1.1 mm. This prevents detection errors in the boundaries with previously scanned portions by repetitively scanning the boundaries.

In FIG. 8, two apertures 35A$a$, 35A$b$ are defined by the electrode 35A. The apertures 35A$a$, 35A$b$ correspond to the measurement points 52A, 53A on the sample 26A. Secondary electron detectors 56A, 57A are placed immediately outside the apertures 35A$a$, 35A$b$. The center of the reference sphere of the electrode 35A is situated above the surface of the sample 26A. Each of the apertures 35A$a$, 35A$b$ is approximately 3 mm wide. The apertures 35A$a$ 35A$b$ preferably are wider than the apertures 36A–36C on the electrode 35 of the FIG.-6 embodiment. When the scanning deflector 25A scans the measurement points 52A, 53B within the scanning regions 54A, 55A, each secondary electron arising from the corresponding measurement points 52A, 53B is incident to the respective aperture 35A$a$, 35A$b$.

Each of the secondary electron detectors 56B, 57B is situated proximally to a respective aperture defined in the electrode 35B, and each of the secondary electron detectors 56C, 57C is situated proximally to a respective aperture defined in the electrode 35C. The electrode 15B detects secondary electrons released from the measurement points within the scanning regions 54B, 55B and the electrode 15C detects secondary electrons released from the measurement points within the scanning regions 54C, 55C.

FIG. 9(a) shows the orientation of the scanning regions 54A–54C and 55A–55C on the sample 26A. A periodic pattern is formed at a pitch PB in the X-direction. The first scanning region group 54A, 55A, the second scanning region 54B, 55B, and the third scanning region 54C, 55C are arranged at the pitch PB in the X-direction. The width DX of each scanning region 54A, 55A, 54B, 55B, 54C, 55C is the same. Each measurement point on the sample (i.e., each convergence point of the primary particles on the surface of the sample 26A) is scanned in the X-direction as shown by an arrow 45.

Returning to FIG. 8, the sample 26A is mounted on a movable stage 28A. A stage drive 29A moves the stage 28A stepwise in the X-direction and continuously in the Y-direction. The positional coordinates of the stage 28A are measured by a laser interferometer (not shown) as known in the art. Data from the laser interferometer are supplied to a main control system 31A. The main control system 31A controls operation of the stage drive 29A by way of a stage driver 32A.

Signals produced by the secondary electron detectors 56A, 57A, 56B, 57B, 56C, 57C are routed through respective waveform shapers 58A, 59A, 58B, 59B, 58C, 59C and then to respective waveform comparators 60A, 61A, 60B, 61B, 60C, 61C. The main control system 31A supplies reference signals to the waveform comparators 60A, 61A, 60B, 61B, 60C, 61C by way of a waveform generator 40A. As shown in FIG. 9(a), because the first scanning-region group 54A, 55A to the third scanning-region group 54C, 55C represent identical portions of the overall pattern, the reference signals supplied by the waveform generator 40A to the waveform comparators 60A, 60B, 60C are identical, and the reference signals supplied to the waveform comparators 61A, 61B, 61C are identical. Thus, the circuit configuration of the waveform generator 40A in this embodiment can be three times less complex than in embodiments in which the reference signals for each scanning-region group must be different from each other. Each of the waveform comparators 60A, 61A, 60B, 61B, 60C, 61C produces an error signal as described above with respect to the waveform comparators 39A–39I of the FIG.-6 embodiment. The waveform comparators 60A, 61A, 60B, 61B, 60C, 61C produce error signals in a manner similar to the waveform comparators 39A–39I described above in the FIG.-6 embodiment, and input the error signals into an error memory 41A from which the main control system 31A can "read" the error signals as required.

This example embodiment operates to conduct inspection of pattern defects on the sample 28A as follows. Each of the irradiation systems 51A, 51B, 51C operates simultaneously to produce a separate charged-particle beam. As the stage 28A moves continuously in the Y-direction, the respective scanning regions 54A and 55A, 54B and 55B, 54C and 55C are irradiated by the corresponding charged-particle beam that is scanned by the respective scanning deflector 25A, 25B, 25C. Thus, as indicated by the arrow 46 in FIG. 9(a), the measurement points that are electrically scanned in the X-direction within each scanning region 54A–55A, 54B–55B, and 54C–55C are also scanned in the positive (+) Y-direction. Meanwhile, the main control system 31A supplies reference data concerning the pattern within the scanning regions to the waveform generator 40A; the waveform generator 40A supplies corresponding reference signals to the waveform comparators 60A–61A, 60B–61B, and 60C–61C. The waveform comparators 60A–61A, 60B–61B, 60C–61C supply any error signals arising in the respective scanning regions 54A–55A, 54B–55B, 54C–55C to the error memory 41C. Pattern-defect inspection is carried out in manner similar to that described with respect to example embodiment 5.

After inspection of the scanning regions 54A–55A, 54B–55B, 54C–55C is complete, the stage 28A moves (steps) in the negative (–) X-direction. As indicated in FIG. 9(b), the sample 26A moves a distance PA/2 in the negative (–) X-direction. Then, the charged-particle beams produced by each of the irradiation systems 51A, 51B, 51C are scanned over regions having the same size as but adjacent to the previously scanned scanning regions (hatched regions in the figure). I.e., the measurement points in each new scanning region (unhatched regions in the figure) are scanned in the X-direction while the stage 28A is continuously moved in the positive (+) Y-direction to scan regions 62A, 63A, 62B, 63B, 64B, 63C, 64C that are adjacent the regions 54A, 55A, 54B, 55B, 54C, 55C, respectively. Again, any error signals that arise are stored in the error memory 41A.

The width DX of each of the scanning regions 54A, 55A and 62A, 63A is 1.1 mm and the gap PA between centers of the scanning regions is 2 mm. Consequently, there is a 0.1-mm scanning overlap of adjacent scanning regions (e.g., of scanning region 54A with scanning region 63A). Such overlaps prevent missing detection of pattern errors in boundary regions between adjacent scanning regions.

Referring to FIG. 10, regions 47A, 47B, 47C represent the sum of the scanned regions 52A, 53A, 62A, 63A; 52B, 53B, 62B, 63B; and 52C, 53C, 62C, 63C, respectively. On the final scan, the stage 28A will only step in the negative (–) X-direction (3/2) PA (e.g., 3 mm in this embodiment). Thus, as shown in FIG. 10, the primary charged-particle beams scan the scanning regions 48A, 49A, 48B, 49B, 48C, 49C and thus complete inspection of the sample 28A. To perform this final scan, the measurement points 52A and 53A, 52B and 53B, 52C and 53C are scanned in the X-direction by the respective deflectors 25A, 25B, 25C, to scan the scanning regions 48A and 49A, 48B and 49B, 48C and 49C in the positive (+) Y-direction by continuously moving the sample 26A in the negative (–) Y-direction.

Because each scanning region on the sample is scanned as a result of both electrical manipulation of the charged-particle beam and mechanical manipulation of the sample (by moving the stage), pattern-defect inspection of the sample can be conducted with high throughput. Moreover, as shown in FIG. 9(a), because the width DX is approximately ½ of the center-to-center dimension PA, secondary electrons from the measurement points 52A, 53A, for example, are accurately incident at the apertures 35Aa, 35Ab of the electrode 35A. This prevents mixing of signals generated by secondary electrons from different measurement points, thereby allowing precise pattern-defect inspections to be made.

Each curved-surface electrode 35A, 35B, 35C in this embodiment preferably defines multiple apertures. Alternatively, when using multiple electrodes, each can define only one aperture if desired. In such an instance, primary charged particles irradiated onto each respective measurement point from the corresponding irradiation system 51A, 51B, 51C carry out the pattern-defect inspection by plural parallel charged-particle beams. Even this alternative arrangement provides an improved throughput over conventional inspection systems.

Although, in this example embodiment, secondary electrons are preferably detected, reflected charged particles can also be detected. This can further improve the S/N ratio of the detection signal.

Therefore, according to this example embodiment, multiple charged-particle beams are irradiated in parallel onto a corresponding multiplicity of measurement points to perform a pattern-defect inspection of a sample at a high throughput.

Example Embodiment 7

Figure 11:
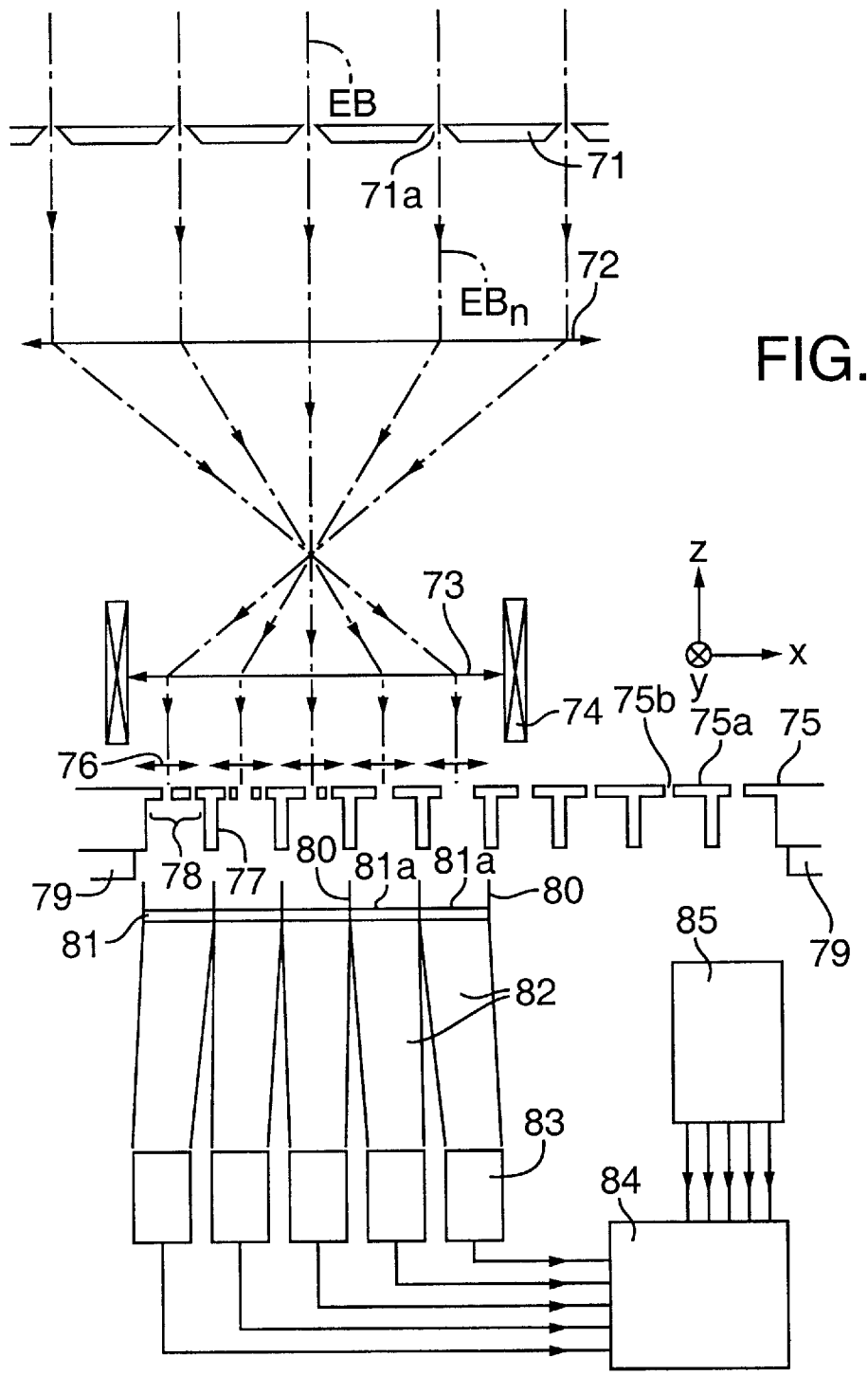
FIG. 11 is a schematic elevational view of a pattern-defect inspection apparatus according to Example Embodiment 7 of the invention.
Figure 12:
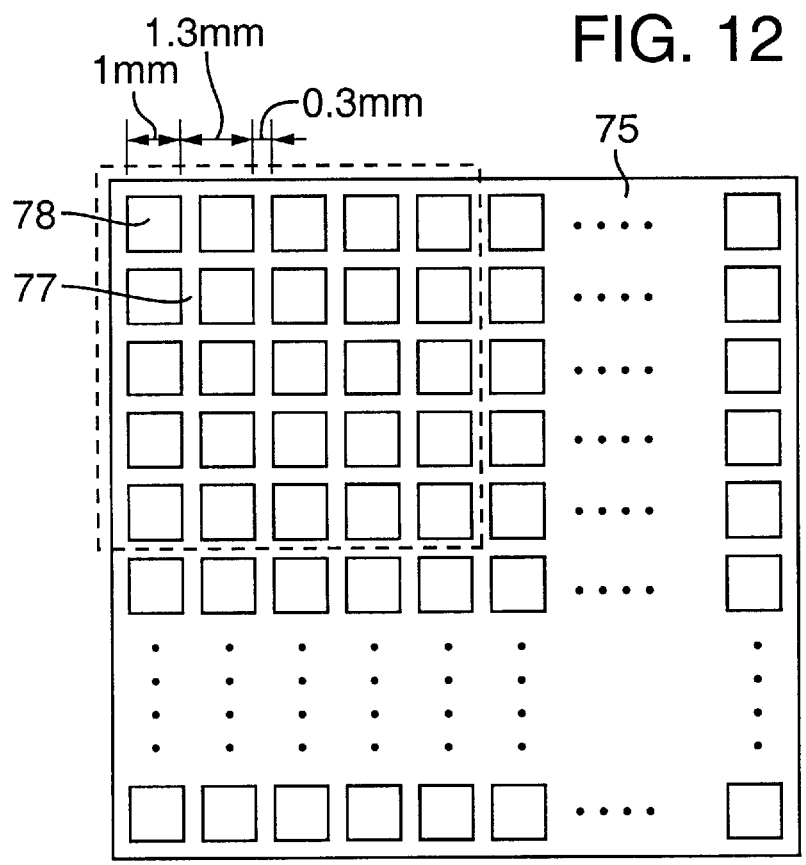
FIG. 12 is an enlarged plan view of a representative sample that is scanned using the FIG. 11 embodiment.

This example embodiment is shown in FIGS. 11 and 12. In FIG. 11, an electron beam EB is used as a representative charged-particle beam produced by an upstream source and condenser lens (not shown but similar to items 1 and 2, respectively, in FIG. 1). The electron beam EB is accelerated to 10 keV toward an aperture plate 71 defining multiple apertures 71a. The apertures 71a produce a corresponding number of electron beams $EB_n$ downstream of the aperture plate 71. By way of example, the apertures 71a are arranged in a matrix of 25 apertures (5 rows×5 columns), with each aperture being 0.2 μm in diameter and separated from adjacent apertures by 5.2 mm. The electron beams $EB_n$ as formed by the aperture plate 71 are parallel to each other. The electron beams EB pass through a first condenser lens 72 and a second condenser lens 73.

The electron beams $EB_n$ then encounter a sample 75 to be tested. The sample 75 is mounted on a sample stage 79 that is operable, by movement of the sample stage 79, to move the sample 75 in the x and y directions.

As shown in FIG. 12, the sample 75 comprises multiple subfields 78. The subfields 78 are divided from one another by cross supports 77. For example, the sample 75 can be a stencil or membrane type mask. As shown in FIG. 11, the sample pattern can be defined by combinations of a "membrane portion" 75a and an "open portion" 75b. By way of example, each subfield can be $(1 \text{ mm})^2$ in area. Each cross-support can be, e.g., 0.3 mm wide.

The electron beams $EB_n$ formed by the aperture plate 71 are reduced by one-fourth by the condenser lenses 72, 73. One image is formed in each of the 25 subfields 78. (FIG. 12 indicates by a dashed line a group of 25 subfields on the sample 75.)

Before encountering the sample 75, the electron beams $EB_n$ pass through a deflector 74 operable to deflect each of the electron beams $EB_n$ a limited amount in the x and y directions. More specifically, the deflector 74 performs a raster scan (arrows 76) of each electron beam $EB_n$ within the limits of, for example, a 1.1 mm area that includes the subfields 78.

Because the amount of electrons that passes through the membrane portion 75a of the sample 75 is approximately 1/10 the amount of electrons that passes through the open portion 75b, an image of the sample pattern can be formed by the electron beams $EB_n$. The image is formed on a scintillator 81. By adjusting the acceleration voltage of the electron beam EB (e.g., an accelerating voltage smaller than approximately 20 kV) such that the electron beams $EB_n$ do not pass through the membrane portion 75a, the contrast of the pattern image can be very good.

The scintillator 81 comprises multiple detection areas 81a, one corresponding to each electron beam $EB_n$. Each detection area 81a has an area of approximately 1 mm. The detection areas 81a are separated from one another by partitions 80 preferably disposed on the upstream-facing surface of the scintillator 81. The partitions 80 prevent the introduction into a particular detection area 81a of electron beams $EB_n$ from adjacent subfields 78. Each detection area 81a of the scintillator 81 generates photons when irradiated by the respective electron beam $EB_n$.

The photons from each detection area 81a are guided to a respective photomultiplier 83 by a respective photoguide 82. Each photomultiplier 83 produces an electrical signal in response to the photons. The electrical signals are routed to a signal processor 84. The signal processor 84 detects any defects in the pattern of the sample 75 by comparing the data encoded in the electrical signals from the photomultipliers 83 with reference data concerning the sample pattern that were previously input into a memory 85.

After scanning of the 25 subfields (i.e., the area within the dashed line of FIG. 12) is complete, the sample stage 79 shifts in the x and y directions as required to place an adjacent group of 25 subfields 78 into position for scanning. Because, in this example embodiment, the subfields 78 have a pitch of 1.3 mm, the sample stage 79 shifts in the x and/or y directions by 5(1.3 mm)=6.5 mm. This sequence of shifting and scanning is repeated until all the subfields of the sample 75 are scanned.

The electron beams $EB_n$ do not pass through the cross-supports 77. As a result, images of the crosssupports 77 are used to precisely align the position of the sample 75 relative to the electron beams $EB_n$, as well as make adjustments in the scanning direction and sensitivity of the electron beams $EB_n$. To correct the position of the sample 75 relative to the electron beams $EB_n$, the deflector 74 can be adjusted to change the deflection angle of the electron beams $EB_n$ passing therethrough and thus avoid producing an image of a cross-support on the scintillator 81. Also, if an image of a cross-support 77 is detected while the subfields 78 are being scanned, then the scan angle can be changed and/or the scanning range can be increased.

In this example embodiment, although a scintillator 81 is preferably used as a charged-particle detector, such detection can be performed using any of various other components such as a photomultiplier, a micro-channel plate, or a PIN diode array.

Although this example embodiment was described above with especial respect to a stencil type mask 75, it will be understood that any of several other types of masks or other samples can be used such as a scattering mask in which the pattern is formed on a thin film such as silicon (Si) by an electron-scattering material such as tungsten (W).

In this example embodiment, it will be understood that the number of apertures 71a defined by the aperture plate 71 is not limited to 25. For example, the number of apertures can be greater to produce a larger number of charged-particle beams EB. A larger number of beams permits a larger area of the sample to be inspected at the same time, thereby reducing the time required to inspect the entire sample.

Whereas the invention has been described in connection with multiple example embodiments, it will be understood that the invention is not limited to those embodiments. On the contrary, the invention is intended to encompass all alternatives, modifications, and equivalents as may be included within the spirit and scope of the invention as defined by the appended claims.

What is claimed is:

1. An apparatus for detecting defects in a pattern on a sample, comprising:

(a) a charged-particle-beam optical system for irradiating multiple charged-particle beams on respective loci in an irradiation region of a surface of the sample so as to cause release of secondary charged particles propagating, during the irradiation, from the loci;

(b) a charged-particle detector situated so as to detect the secondary charged particles propagating from the loci in the irradiated region of the sample; and (c) a multiple-aperture lens defining multiple apertures, each aperture of the lens being situated so as to receive the secondary charged particles propagating from a respective locus in the irradiated region, the multiple-aperture lens being charged and situated relative to the sample so as to attract the secondary charged particles as the secondary charged particles are released from the loci.

2. The apparatus of claim 1, wherein the charged-particle detector is situated so as to detect charged particles passing through the irradiated region of the sample.

3. The apparatus of claim 1, wherein the sample is situated relative to the charged-particle beams such that the charged-particle beams are incident on their respective loci at an oblique angle of incidence.

4. The apparatus of claim 1, wherein the charged-particle detector is configured and situated so as to detect secondary electrons propagating from the loci.

5. The apparatus of claim 4, further comprising an electrode plate, defining multiple apertures, situated so as to capture the secondary electrons propagating from the irradiated region, each aperture of the electrode plate being situated so as to receive secondary electrons released from a corresponding locus in the irradiated region and passing through a respective aperture in the multiple-aperture lens.

6. The apparatus of claim 5, wherein the charged-particle detector comprises a separate detector situated downstream of each aperture of the electrode plate.

7. The apparatus of claim 4, further comprising an electrode plate, defining multiple apertures, situated so as to capture the secondary electrons propagating from the irradiated region, each aperture of the electrode plate being situated so as to receive secondary electrons released from a corresponding locus in the irradiated region.

8. The apparatus of claim 7, wherein the charged-particle detector comprises a separate detector situated downstream of each aperture of the electrode plate.

9. The apparatus of claim 7, wherein the electrode plate is configured to have a spherical profile.

10. The apparatus of claim 9, further comprising a sub-stage deflector, situated beneath the sample, for deflecting the secondary electrons to respective apertures in the electrode plate.

11. The apparatus of claim 4, further comprising:
a signal processor to which each detector is connected;
a comparator to which the signal processor is connected; and
a memory to which the comparator is connected.

12. The apparatus of claim 1, further comprising:
a signal processor to which each detector is connected;
a comparator to which the signal processor is connected; and
a memory to which the comparator is connected.

13. The apparatus of claim 4, further comprising a deflector array comprising multiple deflectors, each deflector in the array being situated so as to receive secondary electrons propagating from a respective locus in the irradiated region.

14. The apparatus of claim 13, further comprising an electrode plate, defining multiple apertures, situated so as to capture the secondary electrons propagating from the irradiated region, each aperture of the electrode plate being situated so as to receive secondary electrons released from a corresponding locus in the irradiated region and passing through a respective deflector of the array.

15. The apparatus of claim 14, wherein the electrode plate is configured to have spherical profile.

16. The apparatus of claim 15, wherein the spherical profile has a center, the center being situated above the surface of the sample.

17. The apparatus of claim 15, further comprising a sub-stage deflector for deflecting the secondary electrons to respective apertures in the electrode plate.

18. The apparatus of claim 1, further comprising a charged-particle-beam source for producing the charged-particle beams and for directing the charged-particle beams toward the sample.

19. The apparatus of claim 18, further comprising a plate situated between the charged-particle-beam source and the sample, the plate defining multiple apertures each forming a respective charged-particle beam for irradiating a respective locus in the irradiated region of the sample.

20. The apparatus of claim 19, wherein the plate is situated so as to be irradiated by a charged-particle flux and, by allowing portions of the charged-particle flux to pass through the apertures, produces the multiple charged-particle beams for irradiating the sample.

21. The apparatus of claim 1, further comprising a scanner for causing the irradiating charged-particle beams to scan respective regions around the loci on the sample.

22. The apparatus of claim 21, wherein the scanner scans multiple charged-particle beams simultaneously on respective loci on the sample.

23. The apparatus of claim 4, further comprising:
multiple charged-particle-beam sources each comprising a charged-particle generator and a plate situated between the generator and a respective irradiated region on the sample, the plate defining multiple apertures each forming a respective charged-particle beam for irradiating a respective locus in the respective irradiated region of the sample; and
for each irradiated region on the sample, a separate electrode plate, defining multiple apertures, situated so as to capture the secondary electrons, propagating from the respective irradiated region, each aperture of the electrode plate being situated so as to receive secondary electrons released from a corresponding locus in the respective irradiated region.

24. A system for inspecting for defects in a pattern on a sample, comprising:
(a) a source of multiple electron beams directed toward the sample, each electron beam having a respective initial propagation axis;
(b) a first lens for focusing each electron beam on a separate respective locus in an irradiation region on a surface of the sample so as to produce secondary electrons upon impingement of the respective electron beam on the locus;
(c) a deflector for simultaneously scanning each electron beam over its respective locus in the irradiation region;
(d) for each electron beam, a detector of secondary electrons released from the respective locus; and
(e) the source of electron beams comprising a plate that defines multiple apertures, each aperture having an optical axis that is shifted relative to the respective initial propagation axis so as to provide each charged-particle beam from the plate to the sample with a propagation path of substantially identical length.

25. The system of claim 24, wherein each electron beam is incident at its respective locus at an oblique angle of incidence.

26. The system of claim 24, further comprising an electrode plate, defining multiple apertures, situated so as to capture the secondary electrons propagating from the irradiated region, each aperture of the electrode plate being situated so as to receive secondary electrons released from a corresponding locus in the irradiated region.

27. The system of claim 26, further comprising a respective deflector for the secondary electrons propagating from each locus, each secondary-electron deflector being for directing the secondary electrons from the locus to the respective aperture in the electrode plate.

28. The system of claim 24, further comprising:
a signal processor to which the detectors are connected, the signal processor being operable to receive electrical signals from each detector based on secondary electrons received by the detector; and a comparator connected to the signal processor, the comparator being operable to receive the processed signals from the detectors and compare them with reference signals so as to detect an error in a pattern defined by the sample at a particular locus.

29. The system of claim 28, further comprising a memory connected to the comparator for storing reference signals and signals from the detectors until needed by the comparator.

30. The system of claim 24, further comprising a respective deflector for the secondary electrons propagating from each locus, each secondary-electron deflector being for directing the secondary electrons from the locus to the respective detector.

31. The system of claim 30, further comprising:

a signal processor to which the detectors are connected, the signal processor being operable to receive electrical signals from each detector based on secondary electrons received by the detector; and a comparator connected to the signal processor, the comparator being operable to receive the processed signals from the detectors and compare them with reference signals so as to detect an error in a pattern defined by the sample at a particular locus.

32. The system of claim 31, further comprising a second lens situated between the sample and the secondary-electron deflector, the second lens comprising a plate defining multiple apertures, each aperture being situated so as to guide the secondary electrons propagating from a respective locus.

33. The system of claim 32, further comprising a shield situated between the second lens and the electrode plate, the shield defining multiple apertures each being situated so as to allow secondary electrons propagating from a respective locus to pass therethrough to the electrode plate.

34. The system of claim 33, further comprising:

a signal processor to which the detectors are connected, the signal processor being operable to receive electrical signals from each detector based on secondary electrons received by the detector; and a comparator connected to the signal processor, the comparator being operable to receive the processed signals from the detectors and compare them with reference signals so as to detect an error in a pattern defined by the sample at a particular locus.

35. A system for inspecting for defects in a pattern defined in a sample, comprising:

(a) a source of multiple electron beams directed toward the sample;

(b) a first lens for focusing each electron beam on a separate respective locus in an irradiation region on a surface of the sample so as to produce secondary electrons upon impingement of the electron beam on the locus;

(c) a deflector for scanning each electron beam over its respective locus in the irradiation region;

(d) a positively biased electrode plate, defining multiple apertures, situated so as to attract the secondary electrons as the secondary electrons are released from the irradiated region, each aperture of the electrode plate being situated so as to receive secondary electrons attracted from a corresponding locus in the irradiated region; and (e) for each electron beam, a detector of secondary electrons released from the respective locus, each detector being situated downstream of the respective aperture in the electrode plate, the detectors being more positively biased than the electrode plate.

36. The system of claim 35, further comprising a sub-stage deflector for deflecting the secondary electrons to respective apertures in the electrode plate.

37. The system of claim 35, wherein the electrode plate has a profile that is a portion of a sphere.

38. The system of claim 35, further comprising:

a waveform shaper connected to each detector and being operable to receive electrical signals from the detector based on secondary electrons received by the detector, to amplify the signals, and to shape the signals for downstream processing;

a waveform comparator connected to each waveform shaper, each waveform comparator being operable to receive the processed signals from the respective waveform shaper and compare them with a reference signal so as to detect an error in a pattern defined by the sample at the respective locus, and to produce an error signal when an error is detected;

a waveform generator, connected to the waveform comparators, for providing reference signals to the waveform comparators;

an error memory connected to the waveform comparators for storing error signals from the waveform comparators corresponding to respective errors found at respective loci; and a main control system connected to the error memory and to the waveform generator for processing the error signals.

39. A system for inspecting for defects in a pattern defined in a sample, comprising:

(a) multiple electron-beam sources, each source being operable to generate multiple electron beams directed toward the sample, each electron-beam source irradiating a respective irradiation region on a surface of the sample;

(b) a lens serving to focus each electron beam on a respective locus in the respective irradiation region so as to produce secondary electrons upon impingement of the electron beam on the locus;

(c) a deflector serving to scan each electron beam over its respective locus;

(d) an electrode plate situated and biased so as to attract secondary electrons as the secondary electrons are released from the loci in the respective irradiation region, each electrode plate defining multiple apertures, wherein the secondary electrons released from the respective locus in the respective irradiation region pass through a respective aperture; and (e) a secondary-electron detector situated downstream of each respective aperture to detect the secondary electrons released from the respective locus.

40. The system of claim 39, further comprising:

a waveform shaper connected to each detector and being operable to receive electrical signals from the detector based on secondary electrons received by the respective detector, to amplify the signals, and to shape the signals for downstream processing;

a waveform comparator connected to each waveform shaper, each waveform comparator being operable to receive the processed signals from the respective waveform shaper and compare them with a reference signal so as to detect an error in a pattern defined by the sample at the respective locus, and to produce an error signal when an error is detected;

a waveform generator, connected to the waveform comparators, for providing reference signals to the waveform comparators;

an error memory connected to the waveform comparators for storing error signals from the waveform comparators corresponding to respective errors found at respective loci; and a main control system connected to the error memory and to the waveform generator for processing the error signals.

41. A system for inspecting for defects in a pattern defined in a sample, comprising:

(a) a source of an electron-beam flux directed toward the sample;

(b) an aperture plate located downstream of the source, the aperture plate defining multiple apertures each for passing a portion of the electron-beam flux so as to produce multiple electron beams;

(c) a lens, located downstream of the aperture plate, for focusing the electron beams on respective loci in an irradiation region of a surface of the sample;

(d) a deflector, located downstream of the lens, for simultaneously scanning each electron beam over a limited area in the irradiation region corresponding to the respective locus;

(e) a scintillator plate, situated downstream of the sample and comprising multiple detection areas each corresponding to a respective locus, each detection area producing photons in response to secondary electrons from the respective locus impinging upon the detection area, the scintillator plate having a positive bias so as to attract the secondary electrons as the secondary electrons are released from the respective loci;

(f) a photoguide situated downstream of each detection area for routing the respective photons to a terminus of the photoguide; and (g) a respective detector situated at the terminus of each photoguide for receiving and detecting the respective photons routed through the respective photoguide and for producing electrical signals in response to detecting the photons.

42. The system of claim 41, further comprising:

a signal processor to which the detectors are connected, the signal processor being operable to compare the signals against corresponding reference signals and to thereby detect an error condition at any of the loci; and an error memory connected to the signal processor, the error memory being operable to store error signals from the signal processor corresponding to respective errors detected at respective loci.

43. A multiple-channel SEM, comprising:

(a) a source of multiple charged-particle beams each directed toward a respective locus in an irradiation region on a surface of a sample;

(b) a charged-particle-beam deflector for scanning each charged-particle beam over a respective scanning region around the respective locus;

(c) a respective detector associated with each scanning region for detecting secondary electrons generated in the scanning region from impingement of the respective charged-particle beam on the respective scanning region, each detector being positively biased and being situated so as to attract secondary electrons as the secondary electrons are released from the respective scanning region.

44. The SEM of claim 43, further comprising an electron lens for guiding secondary electrons from each locus to the respective detector.

45. The SEM of claim 43, wherein each charged-particle beam exhibits an incidence trajectory at the respective locus, each incidence trajectory being different from a normal of the respective charged-particle beam with respect to the surface; and each detector is disposed above a respective secondary-electron axis satisfying a specular reflective condition for the incidence trajectory.

46. The SEM of claim 45, wherein the particle-beam source comprises a source plate defining multiple apertures each having an axis, each axis being shifted such that each incidence trajectory has a similar length from the source plate to the irradiation region.

47. The SEM of claim 43, wherein the particle-beam source comprises a source plate defining multiple apertures, the apparatus further comprising a retention base oriented at a slant relative to the irradiation region, the retention base thus holding the source plate relative to the irradiation surface such that each incidence trajectory has a similar length from the source plate to the irradiation region.

48. The SEM of claim 47, wherein the electron lens is configured as a lens plate defining multiple lens apertures each for secondary electrons propagating from a respective locus, the lens plate defining a portion of a first sphere, and the detectors being disposed on a second sphere concentric with the first sphere and having a radius greater than the first sphere.

49. The SEM of claim 48, further comprising a multiple-aperture electrode plate disposed between the lens plate and the detectors, the electrode plate defining a separate aperture through which pass secondary electrons from a respective locus through a respective lens aperture to a respective detector.

50. The SEM of claim 49, wherein each of the lens apertures has an area, the area of the lens apertures increasing with an increase in an angle between an axis, satisfying the specular reflective condition for the incident charged-particle beams on the surface of the sample, and an axis passing through each respective lens aperture.

51. The SEM of claim 44, further comprising:

an electron deflector situated downstream of the electron lens, the electron deflector being operable to deflect secondary electrons that have passed through the lens apertures of the electron lens; and a controller for controllably energizing the electron deflector in synchrony with energization of the charged-particle-beam deflector such that each secondary electron from a locus is incident to the respective detector.

52. The SEM of claim 51, further comprising a shield situated between the electron lens and the electron deflector, the shield being operable to shield an electrical field produced by the electron deflector.

53. An apparatus for detecting defects in a pattern on a sample, comprising:

(a) an irradiation system operable to irradiate each of multiple loci in an irradiation region on a surface of the sample with a separate charged-particle beam so as to cause each locus to produce secondary electrons;

(b) an electrode having a concave surface oriented toward the irradiation region, the electrode being operable to collect the secondary electrons or reflected charged particles from the sample, the electrode defining multiple apertures each corresponding to and operable to collect secondary electrons produced by a respective locus; and (c) an electron detector situated downstream of each aperture in the electrode for detecting the secondary electrons or reflected charged particles passing through the aperture.

54. The apparatus of claim 53, further comprising:

a charged-particle-beam scanning system for scanning each of multiple charged-particle beams over a respective region associated with each respective locus; and a deflection system for deflecting secondary electrons or reflected charged particles discharged from the sample toward the electrode in synchrony with the charged-particle-beam scanning system.

55. The apparatus of 53, wherein the electrode has a spherical surface having a center that is situated higher than the surface of the sample.

56. The apparatus of claim 53, comprising multiple assemblies each comprising an irradiation system, an electrode, and a detector for simultaneously measuring multiple irradiation regions on the sample.

57. The apparatus of claim 53, wherein each charged-particle beam irradiated onto the irradiation region has a pitch of 1/n, wherein n is a positive integer, or an integral multiple thereof, in which latter instance the sample defines a pattern with periodically repeating regions at a fixed pitch.

58. An apparatus for detecting defects in a pattern on a sample, the sample comprising multiple subfields each defining pattern areas and non-pattern areas, the apparatus comprising:

(a) a source operable to produce multiple charged-particle beams each directed toward a respective locus in a respective subfield on a surface of the sample;

(b) a scanner operable to scan each charged-particle beam about the respective locus within the respective subfield;

(c) a beam accelerator situated and configured to apply an accelerating voltage to the beams for providing the beams with sufficient energy to pass through the non-pattern areas and to pass through the pattern areas more easily than through the non-pattern areas of the respective subfields; and (d) multiple charged-particle detectors each operable to detect the respective charged-particle beam passing through the respective subfield of the sample.

59. The apparatus of claim 58, wherein:

the subfields on the sample are separated from one another by cross-supports; and each charged-particle detector is situated and configured to detect only the respective charged-particle beam transmitted through the respective subfield of the sample.

60. The apparatus of claim 59, wherein the sample is situated relative to the detectors such that the cross supports for a particular subfield block charged particles, from all charged-particle beams except the charged-particle beam passing through the respective subfield, from reaching the respective detector.

61. A method for inspecting a sample defining a pattern, the method comprising:

(a) irradiating each of multiple loci in a region of the sample with a separate charged-particle beam so as to cause the irradiated loci to selectively release secondary charged particles in response to the irradiation;

(b) attracting and collecting the secondary charged particles as they are released from the irradiated loci;

(c) detecting the collected charged particles so as to produce data concerning a characteristic of the pattern at each locus; and (d) processing the data relative to reference data to detect loci in which the pattern has a defect.

62. The method of claim 61, including the step of scanning each of the charged-particle beams over a respective region adjacent each respective locus as the charged-particle beams irradiate the respective loci.

63. An apparatus for detecting defects in a pattern on a sample, comprising:

(a) a charged-particle-beam optical system for irradiating multiple charged-particle beams on respective loci in an irradiation region of a surface of the sample;

(b) a charged-particle detector situated so as to detect secondary electrons propagating, during irradiation, from the loci in the irradiated region of the sample as a result of the charged-particle beams impinging on the loci, the detector being operable to produce data on whether or not the pattern in the irradiated region has any defects; and (c) an electrode plate, configured to have a spherical profile and defining multiple apertures, situated so as to capture the secondary electrons propagating from the irradiated region, each aperture of the electrode plate being situated so as to receive secondary electrons released from a corresponding locus in the irradiated region, wherein the charged-particle detector comprises a separate detector situated downstream of each aperture of the electrode plate.

64. The apparatus of claim 63, further comprising a sub-stage deflector, situated beneath the sample, for deflecting the secondary electrons to respective apertures in the electrode plate.

65. The apparatus of claim 63, wherein the spherical profile has a center, the center being situated above the surface of the sample.

66. A system for inspecting for defects in a pattern defined in a sample, comprising:

(a) a source of multiple electron beams directed toward the sample;

(b) a first lens for focusing each electron beam on a separate respective locus in an irradiation region on a surface of the sample so as to produce secondary electrons upon impingement of the electron beam on the locus;

(c) a deflector for simultaneously scanning each electron beam over its respective locus in the irradiation region;

(d) an electrode plate, having a profile that is a portion of a sphere, the electrode plate defining multiple apertures and being situated so as to attract the secondary electrons propagating from the irradiated region, each aperture of the electrode plate being situated so as to receive secondary electrons released from a corresponding locus in the irradiated region; and (e) for each electron beam, a detector of secondary electrons released from the respective locus, each detector being situated downstream of the respective aperture in the electrode plate.

67. A multiple-channel SEM, comprising:

(a) a source of multiple charged-particle beams each directed toward a respective locus in an irradiation region on a surface of a sample, the particle-beam source comprises a source plate defining multiple apertures;

(b) a charged-particle-beam deflector for scanning each charged-particle beam over a scanning region around the respective locus;

(c) a detector associated with each scanning region for detecting secondary electrons generated in the scanning region from impingement of the respective charged-particle beam on the scanning region; and (d) a retention base oriented at a slant relative to the irradiation region, the retention base thus holding the source plate relative to the irradiation surface such that each incidence trajectory has a similar length from the source plate to the irradiation region.

68. The SEM of claim 67, wherein the electron lens is configured as a lens plate defining multiple lens apertures each for secondary electrons propagating from a respective locus, the lens plate defining a portion of a first sphere, and the detectors being disposed on a second sphere concentric with the first sphere and having a radius greater than the first sphere.

69. The SEM of claim 68, further comprising a multiple-aperture electrode plate disposed between the lens plate and the detectors, the electrode plate defining a separate aperture through which pass secondary electrons from a respective locus through a respective lens aperture to a respective detector.

70. The SEM of claim 69, wherein each of the lens apertures has an area, the area of the lens apertures increasing with an increase in an angle between an axis, satisfying the specular reflective condition for the incident charged-particle beams on the surface of the sample, and an axis passing through each respective lens aperture.

* * * * *

UNITED STATES PATENT AND TRADEMARK OFFICE
CERTIFICATE OF CORRECTION

PATENT NO. : 5,892,224

DATED : April 6, 1999

INVENTOR(S) : Mamoru Nakasuji

It is certified that error appears in the above-identified patent and that said Letters Patent is hereby corrected as shown below:

Column 13, line 37, "16i a" should be --16a--.

Column 13, line 62, "EB1" should be --EB11--.

Column 15, line 25, "elect" should be --shown--.

Column 20, line 23, "(3/2) PA" should be --(3/2) · PA--.

Signed and Sealed this

Twenty-fifth Day of January, 2000

Attest:

*Attesting Officer*　　　　*Acting Commissioner of Patents and Trademarks*